(12) United States Patent
Conrad et al.

(10) Patent No.: US 9,636,034 B2
(45) Date of Patent: May 2, 2017

(54) NON-INVASIVE ANALYTE DETECTION SYSTEM WITH MODULATION SOURCE

(71) Applicant: Verily Life Sciences LLC, Mountain View, CA (US)

(72) Inventors: Andrew Conrad, Mountain View, CA (US); Eric Peeters, Mountain View, CA (US); Vikram Singh Bajaj, Mountain View, CA (US); Jason Thompson, Mountain View, CA (US); Mark Askew, Mountain View, CA (US)

(73) Assignee: Verily Life Sciences LLC, Mountain View, CA (US)

(*) Notice: Subject to any disclaimer, the term of this patent is extended or adjusted under 35 U.S.C. 154(b) by 64 days.

(21) Appl. No.: 14/061,325

(22) Filed: Oct. 23, 2013

(65) Prior Publication Data

US 2015/0112167 A1    Apr. 23, 2015

(51) Int. Cl.
*A61B 5/00* (2006.01)
*A61B 5/05* (2006.01)
(Continued)

(52) U.S. Cl.
CPC .............. *A61B 5/0515* (2013.01); *A61B 5/05* (2013.01); *A61B 5/1455* (2013.01);
(Continued)

(58) Field of Classification Search
None
See application file for complete search history.

(56) References Cited

U.S. PATENT DOCUMENTS

| 4,603,209 A | 7/1986 | Tsien et al. |
| 4,714,763 A | 12/1987 | Theodoropulos |

(Continued)

FOREIGN PATENT DOCUMENTS

| EP | 1 065 250 A1 | 1/1999 |
| EP | 1790977 A1 | 5/2007 |

(Continued)

OTHER PUBLICATIONS

T.D. Merson, S. Castelletto, I. Aharonovich, A. Turbic, T. J. Kilpatrick, A. M. Turnley, "Nanodiamonds with silicon vacancy defects fornon-toxic photostable fluorescent laeling of neural percursor cells", Optics letters, 38:20, 2013.*

(Continued)

*Primary Examiner* — Tse Chen
*Assistant Examiner* — Joanne Hoffman
(74) *Attorney, Agent, or Firm* — McDonnell Boehnen Hulbert & Berghoff LLP

(57) ABSTRACT

A system for modulating a response signal includes functionalized particles configured to interact with target analytes, a detector configured to detect an analyte response signal transmitted from the body, a modulation source configured to modulate the analyte response signal, and a processor configured to non-invasively detect the one or more target analytes by differentiating the analyte response signal from a background signal, at least in part, based on the modulation. The analyte response signal is related to the interaction of the target analytes with the functionalized particles. In some examples, the system may also include magnetic particles and a magnetic field source sufficient to distribute the magnetic particles into a spatial arrangement in the body. The analyte response signal may be differentiated from the background signal, at least in part, based on (Continued)

modulation of the signals due, at least in part, to the spatial arrangement of the magnetic particles.

9 Claims, 29 Drawing Sheets

(51) Int. Cl.
| | |
|---|---|
| *A61B 5/145* | (2006.01) |
| *A61B 5/1455* | (2006.01) |
| A61B 5/0205 | (2006.01) |
| A61B 5/055 | (2006.01) |
| G01R 33/44 | (2006.01) |
| G06F 19/00 | (2011.01) |

(52) U.S. Cl.
CPC .......... *A61B 5/14546* (2013.01); *A61B 5/681* (2013.01); *A61B 5/7228* (2013.01); A61B 5/0022 (2013.01); A61B 5/0071 (2013.01); A61B 5/02055 (2013.01); A61B 5/055 (2013.01); G01R 33/44 (2013.01); G06F 19/3406 (2013.01)

(56) References Cited

U.S. PATENT DOCUMENTS

| | | | |
|---|---|---|---|
| 4,774,339 A | 9/1988 | Haugland et al. | |
| 4,810,636 A | 3/1989 | Corey | |
| 4,812,409 A | 3/1989 | Babb et al. | |
| 4,849,362 A | 7/1989 | DeMarinis et al. | |
| 4,945,171 A | 7/1990 | Haugland et al. | |
| 4,981,977 A | 1/1991 | Southwick et al. | |
| 5,132,432 A | 7/1992 | Haugland et al. | |
| 5,187,288 A | 2/1993 | Kang et al. | |
| 5,227,487 A | 7/1993 | Haugland et al. | |
| 5,242,805 A | 9/1993 | Naleway et al. | |
| 5,248,782 A | 9/1993 | Haugland et al. | |
| 5,268,486 A | 12/1993 | Waggoner et al. | |
| 5,274,113 A | 12/1993 | Kang et al. | |
| 5,433,896 A | 7/1995 | Kang et al. | |
| 5,438,984 A | 8/1995 | Schoendorfer | |
| 5,442,045 A | 8/1995 | Haugland et al. | |
| 5,451,343 A | 9/1995 | Neckers et al. | |
| 5,459,276 A | 10/1995 | Kuhn et al. | |
| 5,478,860 A | 12/1995 | Wheeler et al. | |
| 5,486,616 A | 1/1996 | Waggoner et al. | |
| 5,501,980 A | 3/1996 | Katerinopoulos et al. | |
| 5,569,587 A | 10/1996 | Waggoner | |
| 5,569,766 A | 10/1996 | Waggoner et al. | |
| 5,627,027 A | 5/1997 | Waggoner | |
| 5,696,157 A | 12/1997 | Wang et al. | |
| 5,798,276 A | 8/1998 | Haugland et al. | |
| 5,808,044 A | 9/1998 | Brush et al. | |
| 5,830,912 A | 11/1998 | Gee et al. | |
| 5,846,737 A | 12/1998 | Kang | |
| 5,877,310 A | 3/1999 | Reddington et al. | |
| 6,002,003 A | 12/1999 | Shen et al. | |
| 6,004,536 A | 12/1999 | Leung et al. | |
| 6,008,373 A | 12/1999 | Waggoner et al. | |
| 6,043,025 A | 3/2000 | Minden et al. | |
| 6,127,134 A | 10/2000 | Minden et al. | |
| 6,130,094 A | 10/2000 | Waggoner et al. | |
| 6,130,101 A | 10/2000 | Mao et al. | |
| 6,133,445 A | 10/2000 | Waggoner et al. | |
| 6,162,931 A | 12/2000 | Gee et al. | |
| 6,222,189 B1 * | 4/2001 | Misner ............... | A61B 5/14532 250/341.1 |
| 6,229,055 B1 | 5/2001 | Klaubert et al. | |
| 6,232,130 B1 | 5/2001 | Wolf | |
| 6,339,392 B1 | 1/2002 | Ashihara | |
| 6,562,632 B1 | 5/2003 | Szalecki et al. | |
| 6,615,063 B1 | 9/2003 | Ntziachristos et al. | |
| 6,664,047 B1 | 12/2003 | Haugland et al. | |
| 6,671,527 B2 | 12/2003 | Petersson et al. | |
| 6,716,979 B2 | 4/2004 | Diwu et al. | |
| 6,778,316 B2 | 8/2004 | Halas et al. | |
| 6,974,873 B2 | 12/2005 | Leung et al. | |
| 6,977,305 B2 | 12/2005 | Leung et al. | |
| 7,052,864 B2 | 5/2006 | Durkop et al. | |
| 7,214,190 B1 | 5/2007 | Wilson | |
| 7,236,812 B1 | 6/2007 | Ballerstadt et al. | |
| 7,253,004 B2 | 8/2007 | Vossmeyer et al. | |
| 7,459,145 B2 | 12/2008 | Bao et al. | |
| 7,577,469 B1 | 8/2009 | Aronowitz | |
| 7,701,580 B2 | 4/2010 | Bassler et al. | |
| 7,704,754 B2 | 4/2010 | Malak | |
| 7,763,856 B2 | 7/2010 | Kiesel et al. | |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 7,957,788 B2 | 6/2011 | Judd et al. | |
| 8,153,949 B2 | 4/2012 | Kiesel et al. | |
| 8,217,108 B2 | 7/2012 | Cooper et al. | |
| 8,246,968 B2 | 8/2012 | Zale et al. | |
| 8,268,638 B2 | 9/2012 | Stein et al. | |
| 8,310,676 B2 | 11/2012 | Ikebukuro et al. | |
| 8,323,188 B2 | 12/2012 | Tran | |
| 8,344,054 B2 | 1/2013 | Sun et al. | |
| 8,344,731 B2 | 1/2013 | Lee | |
| 8,349,258 B2 | 1/2013 | Xu et al. | |
| 8,368,402 B2 | 2/2013 | Lee et al. | |
| 8,579,787 B2 | 11/2013 | Shapiro et al. | |
| 8,691,500 B2 | 4/2014 | Kim et al. | |
| 8,790,400 B2 | 7/2014 | Boyden et al. | |
| 8,821,837 B2 | 9/2014 | Perez et al. | |
| 2004/0142025 A1 | 7/2004 | MacLachlan et al. | |
| 2004/0259270 A1 | 12/2004 | Wolf | |
| 2005/0054907 A1 | 3/2005 | Page et al. | |
| 2006/0165805 A1 | 7/2006 | Steinhoff et al. | |
| 2006/0210986 A1 | 9/2006 | Gleich | |
| 2006/0239919 A1 | 10/2006 | Wickline et al. | |
| 2006/0287603 A1 * | 12/2006 | Bartnik et al. ............... | 600/504 |
| 2007/0029195 A1 | 2/2007 | Li et al. | |
| 2007/0255122 A1 | 11/2007 | Vol et al. | |
| 2007/0270672 A1 | 11/2007 | Hayter | |
| 2008/0275318 A1 | 11/2008 | Lastovich et al. | |
| 2008/0305046 A1 | 12/2008 | Hafezi-Moghadam | |
| 2009/0013609 A1 | 1/2009 | Gupta et al. | |
| 2009/0061226 A1 | 3/2009 | Banin et al. | |
| 2009/0149727 A1 * | 6/2009 | Truitt ............... | A61B 5/14552 600/323 |
| 2010/0049010 A1 | 2/2010 | Goldreich | |
| 2010/0204674 A1 | 8/2010 | Forbes et al. | |
| 2010/0259259 A1 | 10/2010 | Zahn et al. | |
| 2010/0261808 A1 | 10/2010 | Schadler et al. | |
| 2011/0027913 A1 | 2/2011 | Bau et al. | |
| 2011/0028803 A1 | 2/2011 | Ollmar | |
| 2011/0117028 A1 | 5/2011 | Zharov | |
| 2011/0140580 A1 | 6/2011 | Yang et al. | |
| 2011/0184259 A1 | 7/2011 | Alarcon et al. | |
| 2011/0245693 A1 | 10/2011 | Hastings et al. | |
| 2011/0251476 A1 | 10/2011 | Gleich et al. | |
| 2012/0041288 A1 | 2/2012 | Essalik | |
| 2012/0052286 A1 | 3/2012 | Norwood et al. | |
| 2012/0164079 A1 | 6/2012 | Sharma | |
| 2012/0172652 A1 | 7/2012 | Dacey et al. | |
| 2012/0252002 A1 | 10/2012 | Pinto De Melo et al. | |
| 2012/0295265 A1 | 11/2012 | Marziali et al. | |
| 2012/0301870 A1 | 11/2012 | Dordick et al. | |
| 2012/0330116 A1 * | 12/2012 | Eggers et al. ............... | 600/314 |
| 2013/0037977 A1 | 2/2013 | Burke et al. | |
| 2013/0046204 A1 | 2/2013 | Lamego et al. | |
| 2013/0123594 A1 | 5/2013 | Tsukada | |
| 2013/0158413 A1 | 6/2013 | Lisogurski et al. | |
| 2013/0251943 A1 | 9/2013 | Pei et al. | |
| 2014/0099007 A1 * | 4/2014 | Sarkar et al. ............... | 382/128 |
| 2014/0099732 A1 * | 4/2014 | Walavalkar et al. ......... | 436/501 |

FOREIGN PATENT DOCUMENTS

| | | |
|---|---|---|
| EP | 1278061 B1 | 2/2011 |
| EP | 2527392 A1 | 11/2012 |

(56) References Cited

FOREIGN PATENT DOCUMENTS

| | | | |
|---|---|---|---|
| EP | 2664192 A1 | 10/2013 | |
| EP | 2698066 A2 | 2/2014 | |
| WO | 97/40104 A1 | 10/1997 | |
| WO | 99/51702 A1 | 10/1999 | |
| WO | 01/05373 A1 | 1/2001 | |
| WO | 01/21624 A1 | 3/2001 | |
| WO | 02/26891 A1 | 4/2002 | |
| WO | 03022360 A2 | 3/2003 | |
| WO | 2005/085339 A1 | 9/2005 | |
| WO | 2008/070459 A2 | 6/2008 | |
| WO | 2008140624 A2 | 11/2008 | |
| WO | WO 2008140624 A2 * | 11/2008 | ............ A61K 49/18 |
| WO | 2009/135325 A1 | 11/2009 | |
| WO | 2010121381 A1 | 10/2010 | |
| WO | 2011/034570 A1 | 3/2011 | |
| WO | 2012071428 A2 | 5/2012 | |
| WO | 2013/013030 A2 | 1/2013 | |
| WO | 2013/109057 A1 | 7/2013 | |
| WO | 2013186628 A1 | 12/2013 | |
| WO | 2014/037498 A2 | 3/2014 | |
| WO | 2014/057432 A2 | 4/2014 | |

OTHER PUBLICATIONS

V. Vaijayanthimala, P Cheng, S Yeh, K Liu, C Hsiao, J Chao, H CHang, "The long-term stability and biocompatibility of fluorescent nanodiamond as an in vivo contrast agent", Biomaterials 33, 2012.*
Smith, A., Dave, S., Nie, S., True, L., Gao, X. "Multicolor quantum dots for molecular diagnostics of cancer", Future Drug Inc, 2006.*
"Multiplex (assay)," downloaded from http://en.wikipedia.org/wiki/Multiplex_(assay) on Sep. 11, 2014.
"FRET Aptamer-Based Glucose Sensor for the Rotating Space BioReactor," SBIR/STTR, downloaded from https://www.sbir.gov/sbirsearch/detail/358185 on Sep. 11, 2014.
Dillow, "Gold Nanosensors Can Be Implanted in the Body to continuously Monitor for Blood Clots and Trace Proteins," Popular Science, downloaded from http://www.popsci.com/science/article/2010-04/gold-nanosensors-continuously-monitor-blood-clots on Jul. 28, 2014.
Eckert, et al., "Novel Molecular and Nanosensors for In Vivo Sensing," Theranostics, vol. 3 (8), pp. 583-594, 2013.
Eckert, et al., "Opening windows on new biology and disease mechanisms: development of real-time in vivo sensors," Interface Focus, vol. 3, No. 3, pp. 1-7, 2013.
"Smart Polymer," downloaded from http://en.wikipedia.org/wiki/Smart_polymer on Aug. 19, 2014.
Jaeel, "Implantable biosensor monitors real-time metabolism of drugs," University of California, Santa Barbara, Medical Apps forum, downloaded from www.imedicalapps.com/2014/02/sensor-realtime-metabolism-drugs.
Li, et al., "Endonuclease-response aptamer-funtionalized hydrogel coating for sequential catch and release of cancer cells," Biomaterials (Abstract), vol. 34 (2), pp. 460-469, 2013.
Song, et al., "Aptamer-based biosensors," Trends in Analytical Chemistry, vol. 27, No. 2, pp. 108-117, 2008.
Battig, "Aptamer-functionalized superporous hydrogels for sequestration and release of growth factors regulated via molecular recognition," Biomaterials (Abstract), vol. 35, Issue 27, pp. 8040-8048, 2014.
Whiteman, Implantable sensor may monitor cancer and diabetes, Medical News Today (2013), downloaded from http://www.medicalnewstoday.com/articles/268347.php on Jul. 28, 2014.
Arruebo, Manuel et al., "Antibody-Conjugated Nanoparticles for Biomedical Applications," Journal of Nanomaterials, vol. 2009 (2009), Article ID 439389, 24 pages (available at http://dx.doi.org/10.1155/2009/439389).
Cherry, Erika et al., "Simulation of Magnetic Particles in the Bloodstream for Magnetic Drug Targeting Applications," 8th International Conference on Multiphase Flow, ICMF 2013, May 26-31, 201, ICMF 2013, Jeju, Korea.
Shapiro, Benjamin "Towards Dynamic Control of Magnetic Fields to Focus Magnetic Carriers to Targets Deep Inside the Body," J Magn Magn Mater May 1, 2009; pp. 1-13.
Shao, Huilin et al, "Magnetic Nanoparticles for Biomedical NMR-based Diagnostics," Beilstein Journal of Nanotechnology, 2010, 1, 142-154.
Liu, Hao-Li et al, "Magnetic Resonance Monitoring of Focused Ultrasound/Magnetic Nanoparticle Targeting Delivery of Therapeutic Agents to the Brain," PNAS Early Edition, 2010, pp. 1-6.
Dubach, et al., "Fluorescent Ion-Selective Nanosensors for Intracellular Analysis with Improved Lifetime and Size", Nano Lett., May 11, 2007, vol. 7(6), pp. 1827-1831, DOI:10.1021/nl0707860. (Abstract only).
Lee, et al., "In Vitro and In Vivo Evaluation of Structure-Stability Relationships of 111In- and 67Ga-labeled Antibody via 1B4M or C-NOTA Chelates", Nuclear Medicine and Biology, Apr. 1997, vol. 24(3), pp. 225-230. (Abstract only).
Ozer, et al., "New Technologies Provide Quantum Changes in the Scale, Speed, and Success of SELEX Methods and Aptamer Characterization", Molecular Therapy Nucleic Acids, Aug. 5, 2014, vol. 3, pp. 1-36, doi:10.1038/mtna2014.34.
Quinn, et al., "Biocompatible, Glucose-Permeable Hydrogel for In Situ Coating of Implantable Biosensiors", Biomaterials, Dec. 1997, vol. 18(24), pp. 1665-1670. (Abstract only).
Quinn, C.P., et al., "Photo-Crosslinked Copolymers of 2-Hydroxyethyl Methacrylate, Poly(ethylene glycol) Tetra-Acrylate and Ethylene Dimethacrylate for Improving Biocompatibility of Biosensors", Biomaterials, Mar. 1995, vol. 16 (5), pp. 389-396. (Abstract only).
Richieri, Gary V., et al.,"A Flourescently Labeled Intestinal Fatty Acid Binding Protein", J. Biol. Chem., Nov. 25, 1992, vol. 267(33), pp. 23495-23501.
Stoltenburg, et al., "SELEX—A (R)evolutionary Method to Generate High-Affinity Nucleic Acid Ligands", Biomolecular Engineering, Jun. 1, 2007, vol. 24, pp. 381-403, doi:10.1016/j.bioeng.2007.06.001.
Ghandehari, H., et al., "Biodegradable and pH Sensitive Hydrogels: Synthesis by a Polymer-Polymer Reaction", J. Macromol. Chem. Phys., Mar. 1996, vol. 197(3), pp. 965-980. (Abstract only).
Ishihara, K., et al., "Glucose Induced Permeation Control of Insulin through a Complex Membrane Consisting of Immobilized Glucose Oxidase and a Poly(amine)", Polymer J., 1984, vol. 16(8), pp. 625-631.
Ruckh, T.T., et al., "Implantable Nanosensors: Toward Continuous Physiologic Monitoring", Anal. Chem., 2014, vol. 86, pp. 1314-1323, dx.doi.org/10.1021/ac402688k.
Search Report and Written Opinion for PCT/US2014/061748 mailed May 6, 2016.
Bagalkot, Vaishali, et al., "Quantum Dot-Aptamer Conjugates for Synchronous Cancer Imaging, Therapy, and Sensing of Drug Delivery Based on Bi-Fluorescence Resonance Energy Transfer", Nano Letters, 2007, vol. 7(10), pp. 3065-3070.
Deng, Y, et al., "Preparation of Magnetic Polymeric Particles Via Inverse Microemulsion Polymerization Process", Journal of Magnetism and Magnetic Materials, Feb. 2003, vol. 257(1), pp. 69-78. (Abstract only).
Eckert, Mark A., et al., "Novel Molecular and Nanosensors for In Vivo Sensing", Theranostics, 2013, vol. 3(8), pp. 583-594.
Estevez, M.C., et al., "Nanoparticle-Aptamer Conjugates for Cancer Cell Targeting and Detection", Methods Mol. Biol., 2010, vol. 624, pp. 235-248. (Abstract only).
Fang, Weijun, et al., "Superparamagnetic Core-Shell Polymer Particles for Efficient Purification of His-Tagged Proteins", Journal of Materials Chemistry, Sep. 7, 2010, vol. 20, pp. 8624-8630. (Abstract only).
Farokhzad, Omid C., et al., "Nanoparticle-Aptamer Bioconjugates for Cancer Targeting", Department of Anesthesiology, Perioperative and Pain Medicine, Expert Opin. Drug Deily., 2006, vol. 3(3), pp. 311-324.
Henry, A., et al., "Continuous Sensing of Blood by Dark-Field Microscopy and Surface-Enhanced Raman Spectroscopy", Nano Science and Technology Institute, 2012, vol. 3(1), pp. 40-43. (Abstract only).

(56) References Cited

OTHER PUBLICATIONS

Kedzierski, Suzy, et al., "Synthetic Antibodies: The Emerging Field of Aptamers", BioProcessing Journal, 2012-2013, pp. 46-49.
Keefe, Anthony D., et al., "Aptamers as Therapeutics", Nature Reviews Drug Discovery, Jul. 2010, vol. 9, pp. 537-550.
Mohanraj, V.J., et al., "Nanoparticles—A Review", Tropical Journal of Pharmaceutical Research, Jun. 2006, vol. 5 (1), pp. 561-573.
Petros, Robby A., et al., "Strategies in the Design of Nanoparticles for Therapeutic Applications", Nature Reviews Drug Discovery, Aug. 2010, vol. 9, pp. 615-627.
Sefah, Kwame, et al., "Development of DNA Aptamers Using Cell-SELEX", Nature Protocols, Jun. 1, 2010, vol. 5, pp. 1169-1185. (Abstract only).
Sun, Jiefang, et al., "A Conjugated Aptamer-Gold Nanoparticle Fluorescent Probe for Highly Sensitive Detection of rHuEPO-a", Sensors, 2011, vol. 11, pp. 10490-10501.
Ulrich, Henning, et al., "DNA and RNA Aptamers: From Tools for Basic Research Towards Therapeutic Applications", Combinatorial Chemistry & High Throughput Screening, Sep. 2006, vol. 9(8), pp. 619-632(14). (Abstract only).
Weinstein, Jason S., et al., "Superparamagnetic Iron Oxide Nanoparticles: Diagnostic Magnetic Resonance Imaging and Potential Therapeutic Applications in Neurooncology and Central Nervous System Inflammatory Pathologies, a Review", Journal of Cerebral Blood Flow & Metabolism, Sep. 16, 2009, vol. 30, pp. 15-35.
Zhang, L., et al., "Nanoparticles in Medicine: Therapeutic Applications and Developments", Clinical Pharmacology & Therapeutics, vol. 83(5), May 2008, pp. 761-769.
"Anti-Thrombin Aptamers", Wikipedia, pp. 1-7. [Retrieved from the Internet Jul. 8, 2014: <URL:http://en.wikipedia.org/wiki/Anti-thrombin_aptamers>].
"Aptamer", Wikipedia, pp. 1-6. [Retrieved from the Internet Jul. 8, 2014:<URL:http://en.wikipedia.org/wiki/Aptamer>].
"Click Chemistry", Wikipedia, pp. 1-6. [Retrieved from the Internet Jul. 8, 2014: <URL:http://en.wikipedia.org/wiki/Click_chemistry>].
"Nanoparticle", Wikipedia, pp. 1-19. [Retrieved from the Internet Jul. 8, 2014: <URL:http://en.wikipedia.org/wiki/Nanoparticle>].
"Optode", Wikipedia, pp. 1-2. [Retrieved from the Internet Jul. 8, 2014:<URL:http://en.wikipedia.org/wiki/Optode>].
"Carboxyl-Adembeads", Ademtech On-line Catalog, pp. 1-3. [Retrieved from the Internet Jul. 8, 2014: <URL:http://www.ademtech.com/products.aspx?id_p=52>].
"Photocleavable Linkers (PC-Linkers)", Ambergen On-line Catalog, pp. 1-4. [Retrieved from the Internet Jul. 8, 2014: <URL:http://www.ambergen.com/technology/pc_linkers.asp>].
"Aptamers", Amsbio On-line Catalog, Accelerate Discovery Through Innovative Life Science, pp. 1-5. [Retrieved from the Internet Jul. 8, 2014:<URL:http://www.amsbio.com/aptamers.aspx>].
"Magnetic Nano and Micro Particles by Chemicell", Chemicell On-line Catalog, pp. 1-2. [Retrieved from the Internet Jul. 8, 2014:<URL:http://www.chemicell.com/home/index.html>].
"EDC: A Water-Soluble Carbodiimide Crosslinker for Zero-Length, Carboxyl-to-Amine Conjugation", Pierce On-line Catalog, pp. 1-4. [Retrieved from the Internet Jul. 8, 2014:<URL:http://www.piercenet.com/product/edc>].
"Modification Highlight: Photo-Cleavable Spacer", Integrated DNA Technologies On-line Catalog, p. 1. [Retrieved from the Internet Jul. 8, 2014:<URL:https://www.idtdna.com/pages/decoded/decoded-articles/core-concepts/decoded/2012/01/10/modification-highlight-photo-cleavable-spacer>].
Shen, Qinglin, et al., "Specific Capture and Release of Circulating Tumor Cells Using Aptamer-Modified Nanosubstrates", Advanced Materials, Mar. 12, 2013, vol. 25(16), pp. 2368-2373.
Bruno, "Fluorescent Nanoparticle-Aptamer-Magnetic Bead Sensor for Bioterrorism Detection in Water", Extramural Research, U.S. Environmental Protection Agency, May 23, 2004. (Abstract).
Ducongé, "In Vivo Screening of Aptamers and Nanoparticles Targeting Tumors Using Optical Imaging", Université Paris Sud. (Abstract).
Farokhzad, et al., "Nanoparticle-Aptamer Bioconjugates: A New Approach for Targeting Prostate Cancer Cells", Cancer Research, Nov. 1, 2004, vol. 64, pp. 7668-7672.
Herr, et al., "Aptamer-Conjugated Nanoparticles for Selective Collection and Detection of Cancer Cells", Analytical Chemistry, May 1, 2006, vol. 78(9), pp. 2918-2924.
Huang, et al., "Aptamer-Functionalized Gold Nanoparticles for Turn-On Light Switch Detection of Platelet-Derived Growth Factor", Analytical Chemistry, May 26, 2007, vol. 79(13), pp. 4798-4804.
Reinemann et al., "Aptamer-Modified Nanoparticles and their Use in Cancer Diagnostics and Treatment", Swiss Medical Weekly, Jan. 6, 2014, vol. 144, w13908, doi:10.4414/smw.2014.13908.
Wang, et al., "Aptamer Biosensor for Protein Detection Using Gold Nanoparticles", Analytical Biochemistry, 2008, vol. 373, pp. 213-219, doi:10.1016/j.ab.2007.11.013.
Zhang, et al., "Development of Smart Nanoparticle-Aptamer Sensing Technology", Faraday Discuss., 2011, vol. 149, pp. 319-332. (Abstract).
Zhang, Jiani, et al., "Aptamer-Conjugated Gold Nanoparticles for Bioanalysis", Nanomedicine, 2013, vol. 8(6), pp. 983-993, doi: 10.2217/nnm.13.80. (Abstract).
"DNA Aptamer Conjugated Gold Nanoparticle for Targeting Cancer Cells", IIT Mandi, 2011, [Retrieved from the Internet May 6, 2014: <URL:http://www.iitmandi.ac.in/research/nanoparticle.html>].
International Search Report for PCT/US2014/061748 mailed Jan. 29, 2015.
Merson, T.D., et al., "Nanodiamonds with Silocon Vacancy Defects for Non-Toxic Photostable Fluorescent Labeling of Neural Precursor Cells", Opt. Lett., Oct. 15, 2013, vol. 38(20), pp. 4170-4173, doi:10.1364/OL.38.004170.
Vaijayanthimala, V., et al., "The Long-Term Stability and Biocompatibility of Fluorescent Nanodiamond as an In Vivo Contrast Agent", Biomaterials, Jun. 28, 2012, vol. 33, pp. 7794-7802, http://dx.dio.org/10.1016/j.biomaterials.2012.06.084.
Johnson, C., et al., "Magnetic Relaxometry with an Atomic Magnetometer and SQUID Sensors on Targeted Cancer Cells", J. Magn Magn Mater., Aug. 1, 2012, vol. 324(17), pp. 2613-2619, doi:10.1016/j.jmmm.2012.03.015.
Anker, Jeffrey N. et al., Magnetically Modulated Optical Nanoprobes, The University of Michigan Chemistry Department, Ann Arbor, Michigan 48109-1055, Applied Physics Letters, vol. 82, No. 7, Feb. 17, 2013, pp. 1102-1104.
Behrend, Caleb J. et al., Metal-Capped Brownian and Magnetically Modulated Optical Nanoprobes (MOONs): Micromechanics in Chemical and Biological Microenvironments, J. Phys. Chem. B 2004, 108, 10408-10414.
Chaturvedi, P. et al., Emerging Technologies for Non-Invasive Quantification of Physiological Oxygen Transport in Plants, Birck and NCN Publications, Birck Nanotechnology Center, Planta (2013) 238:599-614, DOI 10.1007/s00425-013-1926-9, http://docs.lib.purdue.edu/nanopub/1455.

\* cited by examiner

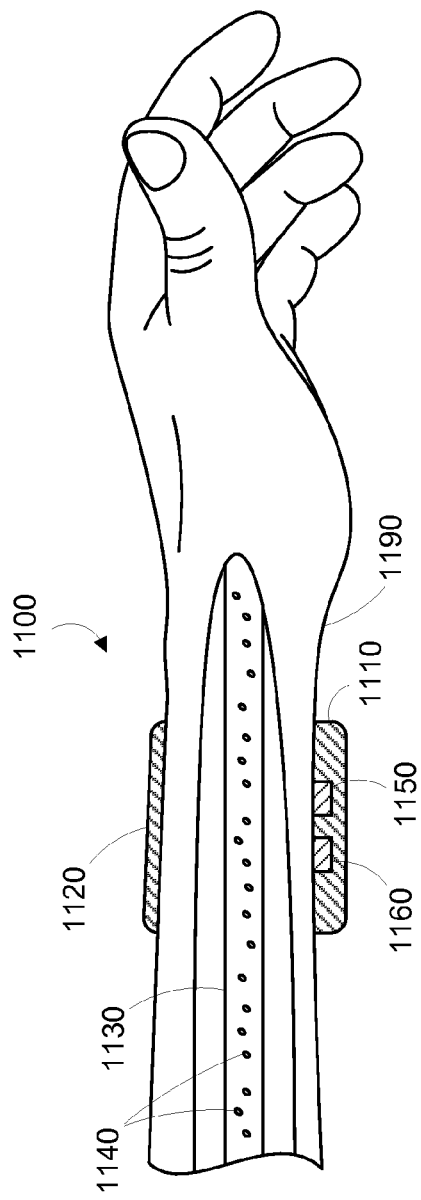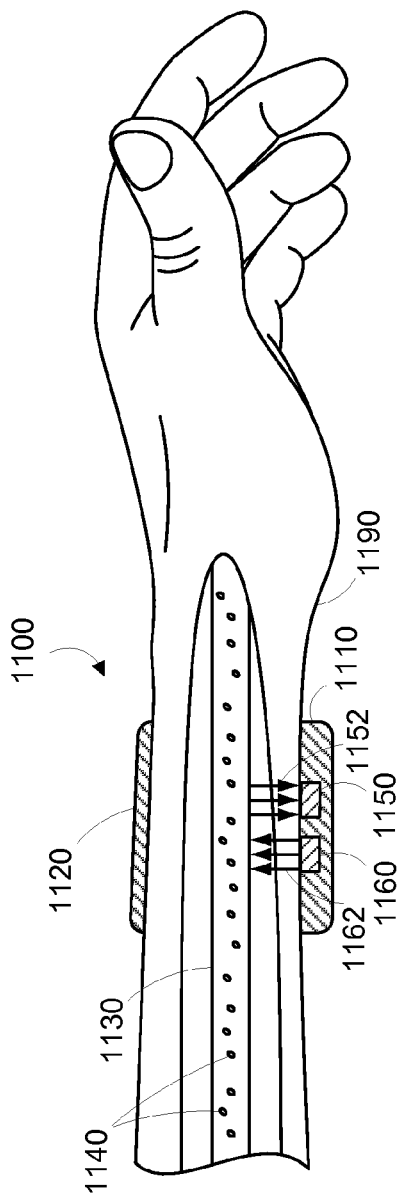

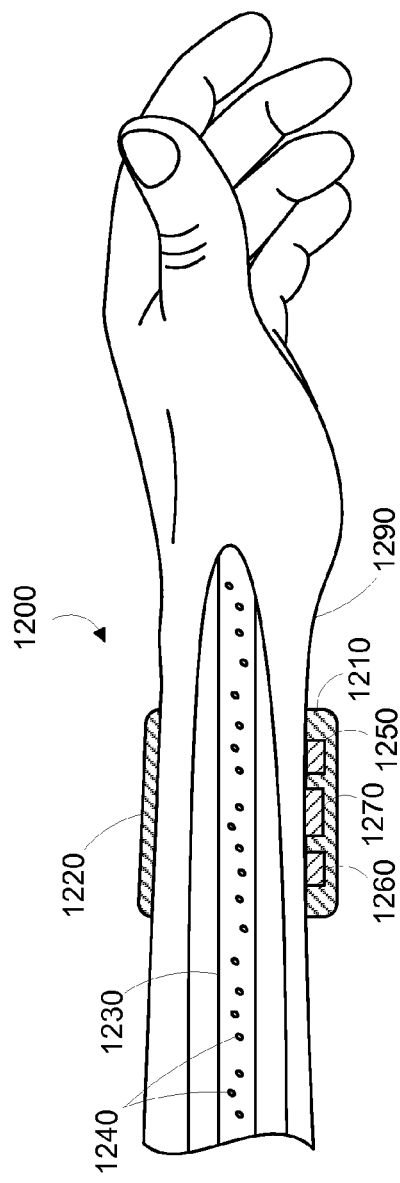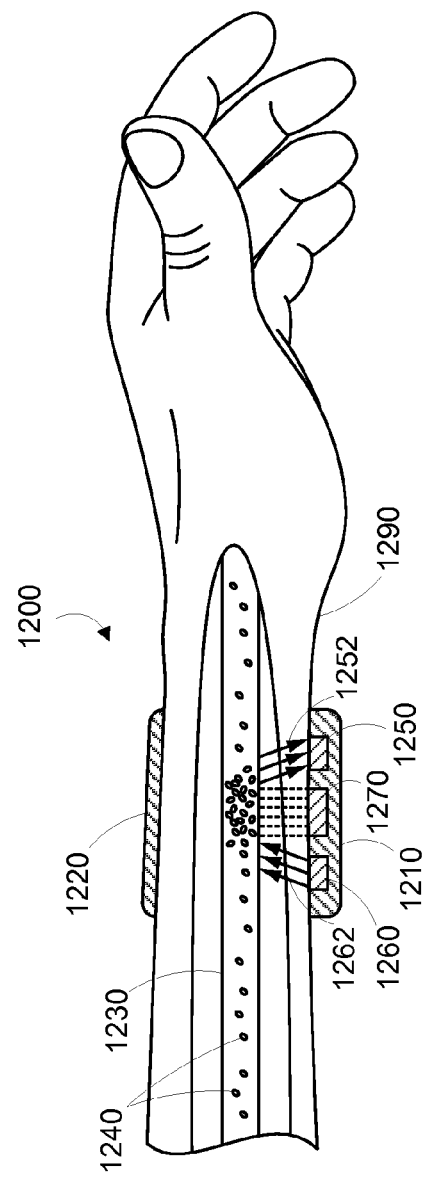

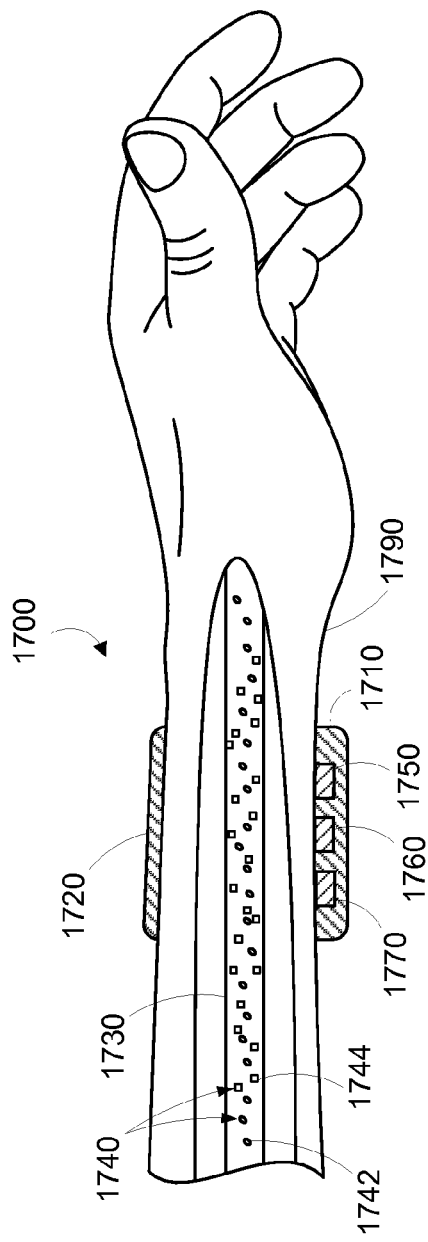
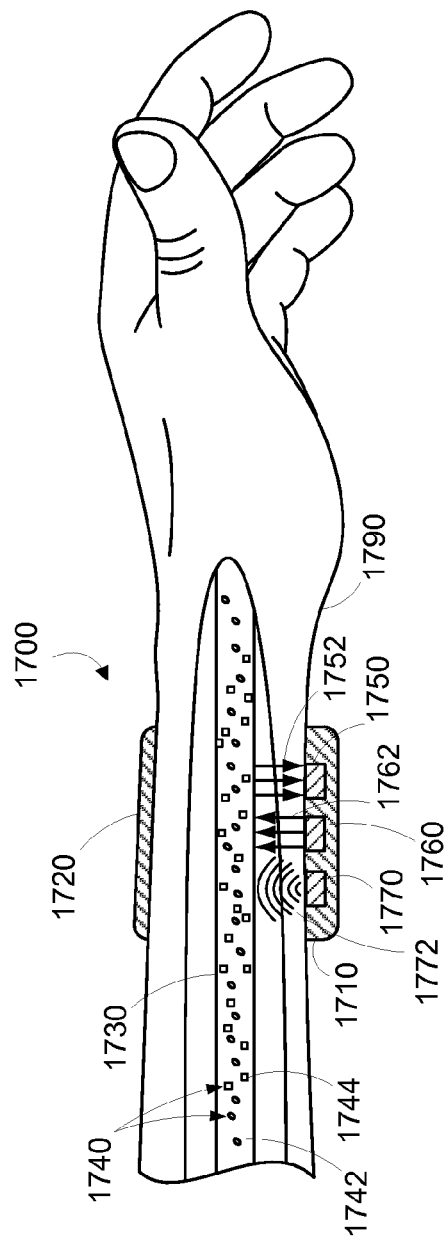

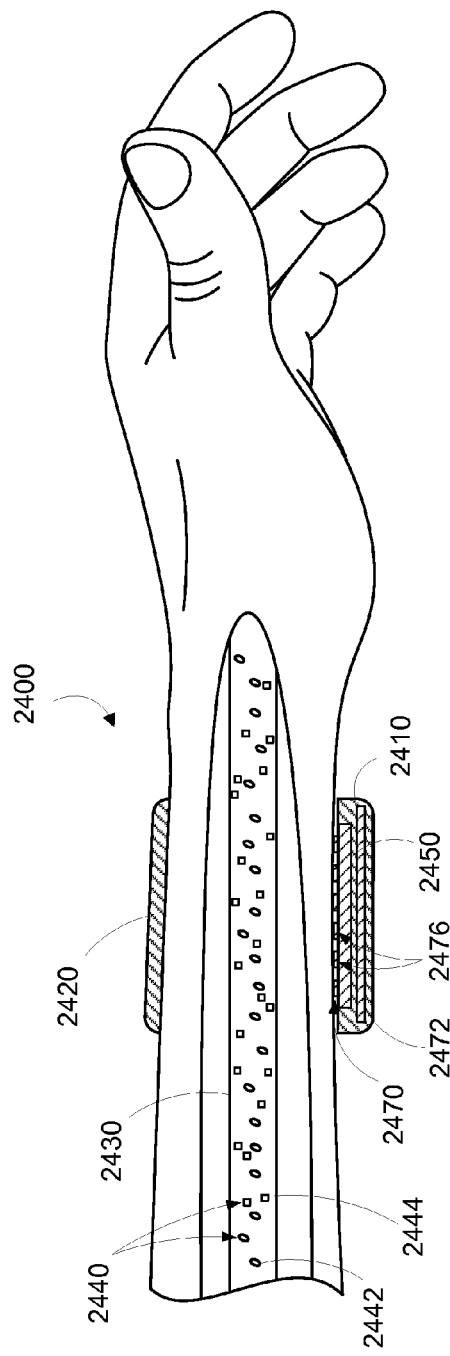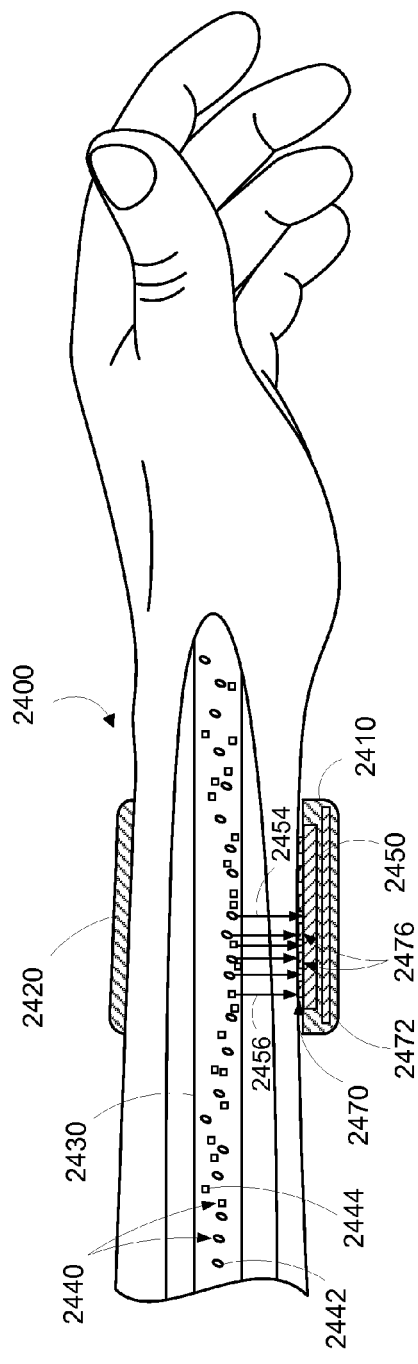

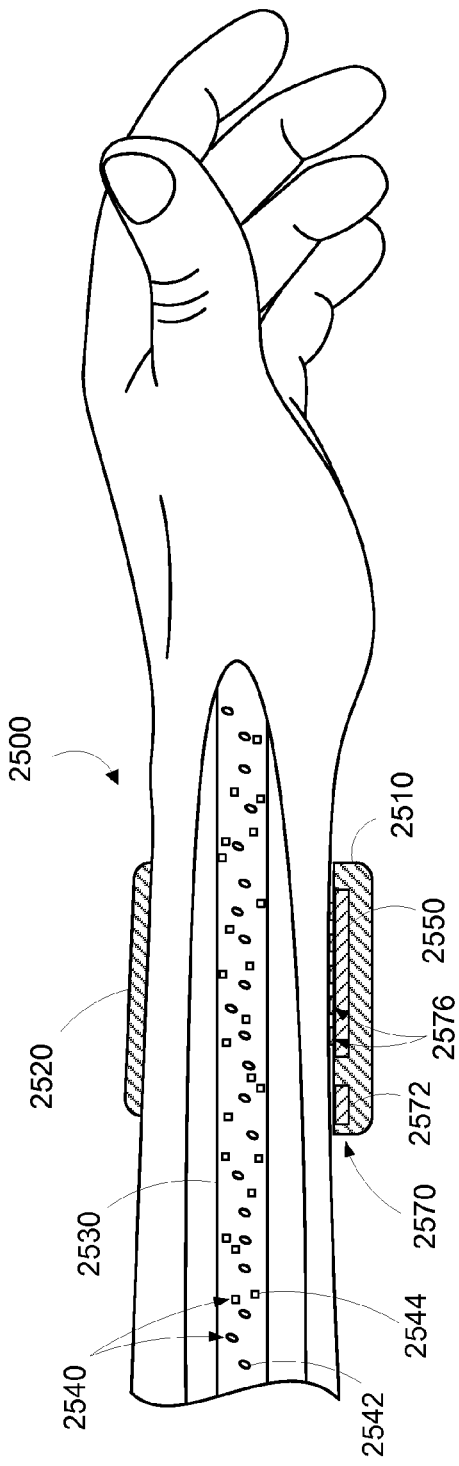
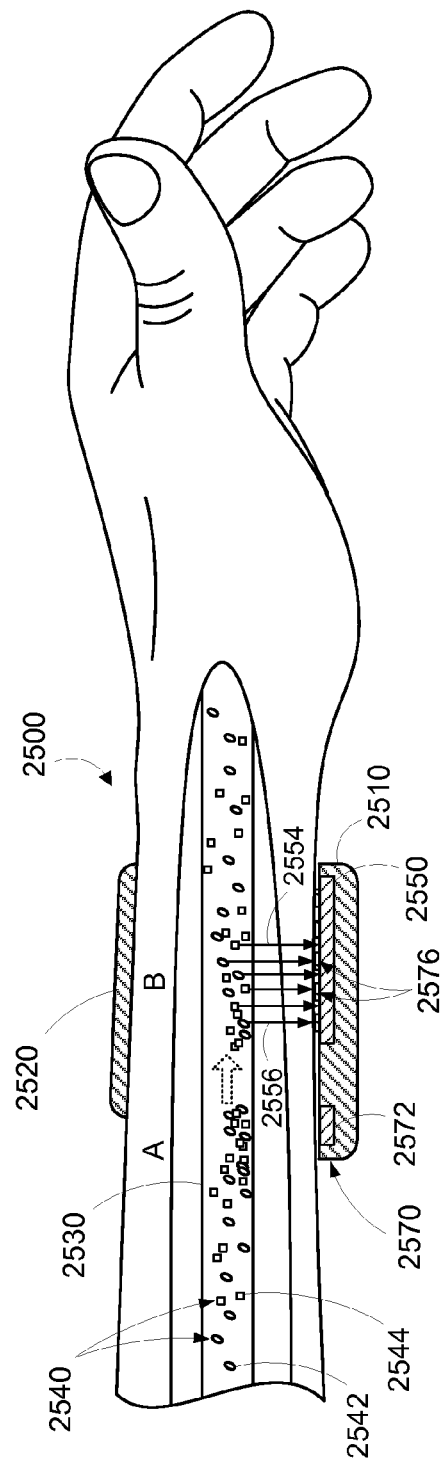

NON-INVASIVE ANALYTE DETECTION SYSTEM WITH MODULATION SOURCE

BACKGROUND

Unless otherwise indicated herein, the materials described in this section are not prior art to the claims in this application and are not admitted to be prior art by inclusion in this section.

A number of scientific methods have been developed in the medical field to evaluate physiological conditions of a person by detecting and/or measuring one or more analytes in a person's blood or other bodily fluids or tissues. The one or more analytes could be any analytes that, when present in or absent from the blood, or present at a particular concentration or range of concentrations, may be indicative of a medical condition or health state of the person. The one or more analytes could include enzymes, reagents, hormones, proteins, cells or other molecules, such as carbohydrates, e.g., glucose.

In a typical scenario, a person's blood is drawn and either sent to a lab or input into a handheld testing device, such as a glucose meter, where one or more tests are performed to measure various analyte levels and parameters in the blood. For most people, the blood tests are infrequent, and an abnormal analyte level indicative of a medical condition may not be identified until the next blood test is performed. Even in the case of relatively frequent blood testing, such as may be found with those with diabetes, who regularly draw blood to test for blood glucose concentration, those blood tests are typically performed when the user is awake, although the blood glucose levels (and potential variations in such levels) occurring during the night could provide important information to assist a physician in assessing that person's medical condition. Further, most known methods of analyte detection and analysis require the collection of blood or other bodily fluid samples, which may be inconvenient, invasive and require significant patient compliance.

Moreover, some blood analytes are particularly difficult to identify and quantify with conventional sensing techniques. For small or rarified analytes, such as circulating tumor cells, for example, only 1 such cell may be present in 10 mL of blood. Impractically large quantities of blood would have to be drawn or otherwise sampled and analyzed in order to catch such cells with statistical significance.

Methods for analyte detection and characterization often suffer from a low signal-to-noise ratio (SNR), since the signal obtained from the analyte (in general, a small object) is typically weak in comparison to the background. This can make discerning between target analytes present in the blood, versus other analytes, particles, and tissues, etc. present in the blood and elsewhere in the body can be very difficult, especially where the measurements are taken non-invasively from outside the body. This is particularly true with some methods of analyte characterization, such as optical methods, or where the target analytes are rare in the blood or are of a relatively small size. Accordingly, such measurements can be much more time consuming (if a large volume of blood must be analyzed), less sensitive, less specific and generally less informative on the whole. For example, with fluorescence detection techniques, it is often difficult to obtain highly sensitive measurements of a target analyte because other tissues, cells, and molecules in the body may have some inherent fluorescent properties, creating a high level of background noise.

SUMMARY

Some embodiments of the present disclosure provide a system including: (i) functionalized particles, wherein the functionalized particles are configured to interact with one or more target analytes present in an environment; (ii) a detector configured to detect an analyte response signal transmitted from the environment, wherein the analyte response signal is related to the interaction of the one or more target analytes with the functionalized particles; (iii) a modulation source configured to modulate the analyte response signal; and (iv) a processor configured to non-invasively detect the one or more target analytes by differentiating the analyte response signal from a background signal, at least in part, based on the modulation.

Further embodiments of the present disclosure provide a system including: (i) functionalized particles, wherein the functionalized particles are configured to interact with one or more target analytes present in an environment; (ii) a detector configured to detect a response signal transmitted from the environment, wherein the response signal includes a background signal and an analyte response signal related to the interaction of the one or more target analytes with the functionalized particles; (iii) magnetic particles; (iv) a magnetic field source sufficient to distribute the magnetic particles into a spatial arrangement in the environment; and (v) a processor configured to non-invasively detect the one or more target analytes by differentiating the analyte response signal from the background signal, at least in part, based on modulation of the signals due, at least in part, to the spatial arrangement of the magnetic particles.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 11A is side partial cross-sectional view of a wrist-mounted device, while on a human wrist.

FIG. 11B is side partial cross-sectional view of a wrist-mounted device, while on a human wrist.

FIG. 12A is side partial cross-sectional view of a wrist-mounted device, while on a human wrist.

FIG. 12B is side partial cross-sectional view of a wrist-mounted device, while on a human wrist.

FIG. 17A is side partial cross-sectional view of a wearable device, while on a human wrist, illustrating use of an example modulation source.

FIG. 17B is side partial cross-sectional view of a wearable device, while on a human wrist, illustrating use of an example modulation source.

FIG. 24A is side partial cross-sectional view of a wearable device, while on a human wrist, illustrating use of an example modulation source.

FIG. 24B is side partial cross-sectional view of a wearable device, while on a human wrist, illustrating use of an example modulation source.

FIG. 25A is side partial cross-sectional view of a wearable device, while on a human wrist, illustrating use of an example modulation source.

FIG. 25B is side partial cross-sectional view of a wearable device, while on a human wrist, illustrating use of an example modulation source.

DETAILED DESCRIPTION

Figure 1:
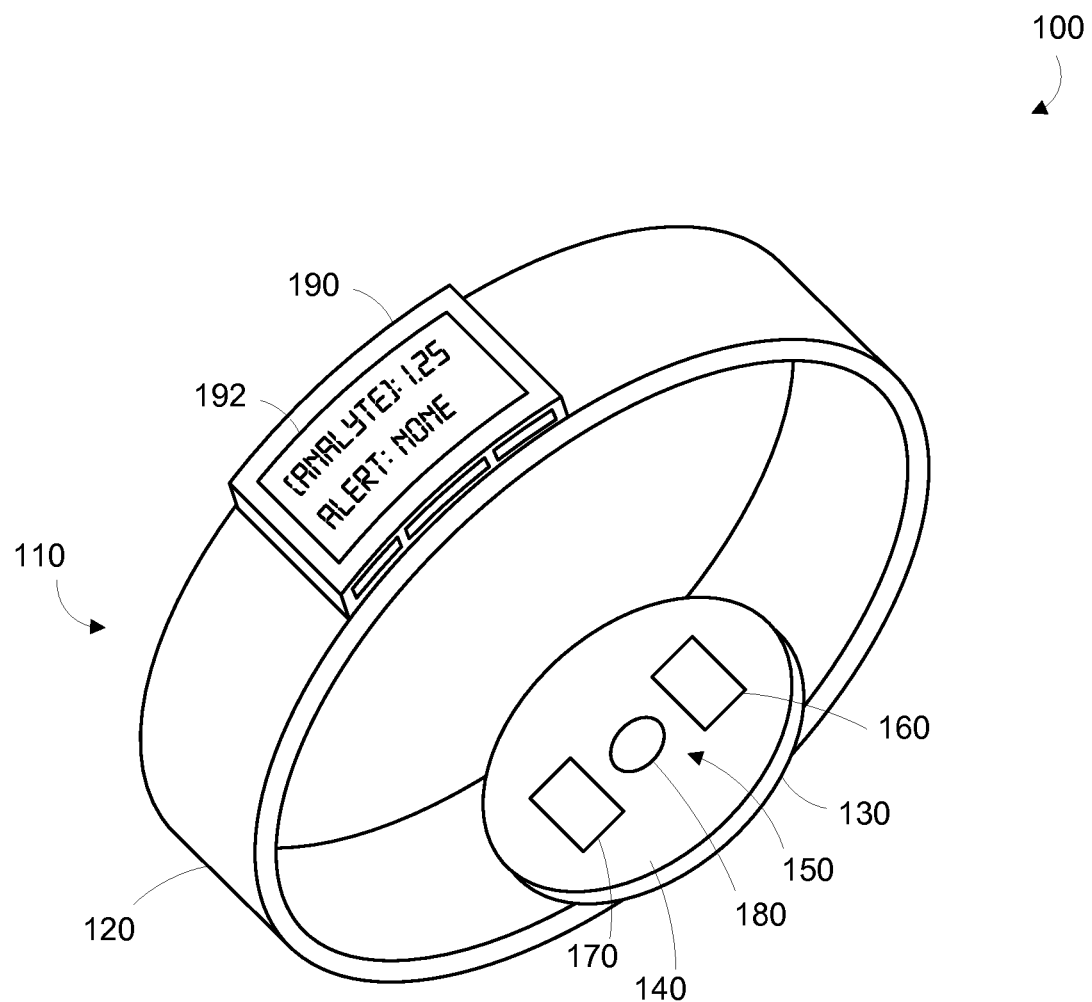
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. Overview

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The one or more analytes could be any analytes that, when present in or absent from the blood, or present at a particular concentration or range of concentrations, may be indicative of a medical condition or health of the person. For example, the one or more analytes could include enzymes, hormones, proteins, cells or other molecules.

In an example embodiment, the system obtains at least some of the health-related information by detecting the binding or interaction of a clinically-relevant analyte to or with particles, for example, microparticles or nanoparticles, introduced into a lumen of the subsurface vasculature that have been functionalized with a receptor that has a specific affinity to bind to or interact with the specific analyte. The term "binding" is understood in its broadest sense to also include a detectable interaction between the clinically relevant analyte and the functionalized particles. The functionalized particles can be introduced into the person's blood stream by injection, ingestion, inhalation, transdermally, or in some other manner.

The particles can be functionalized by covalently or otherwise attaching or associating a receptor that specifically binds or otherwise interacts with a particular clinically-relevant analyte. The functionalized receptor can be an antibody, peptide, nucleic acid, phage, bacteria, virus, aptamer or any other molecule with a defined affinity for a target analyte. Additionally or alternatively, the receptor may be inherent to the particle itself. For example, the particle itself may be a virus or a phage with an inherent affinity for certain analytes. Other compounds or molecules, such as fluorophores or autofluorescent or luminescent markers or non-optical contrast agents (e.g. acoustic impedance contrast, RF contrast and the like), which may assist in interrogating the particles in vivo, may also be attached to the particles.

The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. Those of skill in the art will understand a "particle" in its broadest sense and that it may take the form of any fabricated material, a molecule, cryptophan, a virus, a phage, etc. Further, a particle may be of any shape, for example, spheres, rods, non-symmetrical shapes, etc.

In some examples, the particles may also be magnetic and can be formed from a paramagnetic, super-paramagnetic or ferromagnetic material or any other material that responds to a magnetic field. Alternatively, the particles may also be made of non-magnetic materials such as polystyrene. Where magnetic particles are used, the system may include a magnet that can direct into the portion of subsurface vasculature a magnetic field that is sufficient to manipulate functionalized magnetic particles in a lumen of that portion of subsurface vasculature, for example, to collect or slow down in a certain area. However, measurements may be taken without localized "collection" of the functionalized particles. The system may be configured to activate the magnetic periodically, such as at certain times of the day (e.g., every hour).

The system may further include one or more data collection systems for interrogating, in a non-invasive manner, the functionalized particles present in a lumen of the subsurface vasculature in a particular local area. In one example, the system includes a detector configured to detect a response signal transmitted from a portion of subsurface vasculature. The response signal can include both an analyte response signal, which can be related to the interaction of the one or more target analytes with the functionalized particles, and a background noise signal. For example, the functionalized particles may include a chemiluminescent marker configured to produce a response signal in the form of luminescence radiation produced in response to a chemical reaction initiated, at least in part, to the binding of the target analyte to the particle.

In some examples, the system may also include an interrogating signal source for transmitting an interrogating signal that can penetrate into a portion of subsurface vasculature, or another body system, and a detector for detecting a response signal that is transmitted from the portion of subsurface vasculature, or other body system, in response to the interrogating signal. The interrogating signal can be any kind of signal that is benign to the patient, such as electromagnetic, magnetic, optic, acoustic, thermal, mechanical, electric and results in a response signal that can be used to measure a physiological parameter or, more particularly, that can detect the binding or interaction of the clinically-relevant analyte to the functionalized particles. In one example, the interrogating signal is a radio frequency (RF) signal and the response signal is a magnetic resonance signal, such as nuclear magnetic resonance (NMR). In another example, where the functionalized particles include a fluorophore, the interrogating signal is an optical signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector. In another example, where the functionalized particles include an electrically conductive material or a magnetically lossy material, the interrogation signal may be a time-varying magnetic field or a radio frequency (RF) electromagnetic signal, with sufficient signal power to rapidly heat the particles. The response signal may be an acoustic emission from the particles, caused by rapid thermal expansion of the particles, or caused by cavitation of the liquid medium in contact with the particles. As described above, in some cases, an interrogating signal may not be necessary to produce an analyte response signal.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to functionalized particles bound to or interacting with target analyte(s)—and an "unbound" particle signal—related to functionalized particles not bound to or interacting with target analyte(s). For example, in some measurement or characterization schemes, it may be useful or necessary to determine the percentage of functionalized particles introduced into the body that have bound to the target analyte. In such cases, the modulation source may be configured to modulate the analyte response signal differently than the unbound particle signal.

The elements of the system, namely the type of modulation, the type/shape/materials of particles, types of receptors and target analytes may all be interrelated. Ultimately, the type of particle and receptor used to detect a particular target analyte may be dictated, to some extent, by the characteristics of the target analyte (i.e., type, size, shape, affinities, etc.), the chosen type of modulation (i.e., spatial, spectral, thermal, magnetic, mechanical, chemical, etc.), and the mode of interrogation (optical, acoustic, magnetic, RF, etc.).

Data collected by the detector may be sent to a processor for analysis. The processor may be configured to non-invasively detect the one or more target analytes by differentiating the analyte response signal from the background noise signal based, at least in part, on the modulation. In some cases, the processor may further be configured to differentiate the analyte response signal from the unbound particle signal. Further, the processor may be configured to determine the concentration of a particular target analyte in the blood from, at least in part, the analyte response signal. The detection and concentration data processed by the processor may be communicated to the patient, transmitted to medical or clinical personnel, locally stored or transmitted to a remote server, the cloud, and/or any other system where the data may be stored or accessed at a later time.

The processor may be located on an external reader, which may be provided as an external body-mounted device, such as a necklace, wristwatch, eyeglasses, a mobile phone, a handheld or personal computing device or some combination thereof. Data collected by the detector may be transmitted to the external reader via a communication interface. Control electronics can wirelessly communicate the data to the external reader by modifying the impedance of an antenna in communication with the detector so as to characteristically modify the backscatter from the antenna. In some examples, the external reader can operate to intermittently interrogate the detector to provide a reading by radiating sufficient radiation to power the detector to obtain a measurement and communicate the result. In this way, the external reader can acquire a series of analyte identification and concentration measurements over time without continuously powering the detector and/or processor. The processor may also be provided at another location distal to the detector, and the detector data is communicated to the processor via a wired connection, a memory card, a USB device or other known method. Alternatively, the processor may be located proximal to the detector and may be configured to locally analyze the data that it collects and then transmit the results of the analysis to an external reader or server.

The external reader may include a user interface, or may further transmit the collected data to a device with a user interface that can indicate the results of the data analysis. In this way, the person wearing, holding or viewing the device can be made aware of the nutritional analysis and/or potential medical conditions. The external reader may also be configured to produce an auditory or tactile (vibration) response to alert the patient of a medical condition. Further, the external reader may also be configured to receive information from the patient regarding his/her health state, wellness state, activity state, nutrition intake and the like, as additional input information to the processor. For example, the user may input a health or wellness state, such as, experiencing migraine symptoms, jittery, racing heart, upset stomach, feeling tired, activity state including types and duration of physical activity nutrition intake including meal timing and composition, and other parameters including body weight, medication intake, quality of sleep, stress level, personal care products used, environmental conditions, social activity, etc. Further, the reader may also receive signals from one or more other detectors, such as a pedometer, heart rate sensor, blood pressure sensor, blood oxygen saturation level, body temperature, GPS or other location or positioning sensors, microphone, light sensor, etc.

The system may be configured to obtain data during pre-set measurement periods or in response to a prompt. For example, the system may be configured to operate the detector and collect data once an hour. In other examples, the system may be configured to operate the detector in response to a prompt, such as a manual input by the patient or a physician. The system may also be configured to obtain data in response to an internal or external event or combination of events, such as during or after physical activity, at rest, at high pulse rates, high or low blood pressures, cold or hot weather conditions, etc. In other examples, the system could operate the detector more frequently or less frequently, or the system could measure some analytes more frequently than others.

Data collected by the system may be used to notify the patient of, as described above, analyte levels or of an existing or imminent medical emergency. In some examples, the data may be used to develop an individual baseline profile for the patient. The baseline profile may include patterns for how one or more of the patient's analyte levels typically change over time, such as during the course of a day, a week, or a month, or in response to consumption of a particular type of food/drug. The baseline profile, in essence, may establish "normal" levels of the measured analytes for the patient. Additional data, collected over additional measurement periods, may be compared to the baseline profile. If the additional data is consistent with the patterns embodied in the baseline profile, it may be determined that the patient's condition has not changed. On the other hand, if the additional data deviates from the patterns embodied in the baseline profile, it may be determined that the patient's condition has changed. The change in condition could, for example, indicate that the patient has developed a disease, disorder, or other adverse medical condition or may be at risk for a severe medical condition in the near future. Further, the change in condition could further indicate a change in the patient's eating habits, either positively or negatively, which could be of interest to medical personnel. Further, the patient's baseline and deviations from the baseline can be compared to baseline and deviation data collected from a population of wearers of the devices.

When a change in condition is detected, a clinical protocol may be consulted to generate one or more recommendations that are appropriate for the patient's change in condition. For example, it may be recommended that the patient inject himself/herself with insulin, change his/her diet, take a particular medication or supplement, schedule an appointment with a medical professional, get a specific medical test, go to the hospital to seek immediate medical attention, abstain from certain activities, etc. The clinical protocol may be developed based, at least in part, on correlations between analyte concentration and health state derived by the server, any known health information or medical history of the patient, and/or on recognized standards of care in the medical field. The one or more recommendations may then be transmitted to the external reader for communication to the user via the user interface.

Correlations may be derived between the analyte concentration(s) measured by the system and the health state reported by the patient. For example, analysis of the analyte data and the health state data may reveal that the patient has experienced certain adverse health conditions, such as a migraine or a heart attack, when an analyte reaches a certain concentration. This correlation data may be used to generate recommendations for the patient, or to develop a clinical protocol. Blood analysis may be complemented with other physiological measurements such as blood pressure, heart rate, body temperature etc., in order to add to or enhance these correlations.

Further, data collected from a plurality of patients, including both the analyte measurements and the indications of health state, may be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

The above described system may be implemented as a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Example Wearable Devices

A wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house the data collection system 150, which may include at least one detector 160 for detecting at least one physiological parameter, which could include any parameters that may relate to the health of the person wearing the wearable device. For example, the detector 160 could be configured to measure blood pressure, pulse rate, respiration rate, skin temperature, etc. At least one of the detectors 160 is configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 100 may not include a signal source 170. For example, the functionalized particles include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemiluminescent marker configured to produce a response signal in the form of luminescence radiation produced in response to a chemical reaction initiated, at least in part, to the binding of the target analyte to the particle.

A collection magnet 180 may also be included in the data collection system 150. In such embodiments, the functionalized particles may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

Figure 2A:
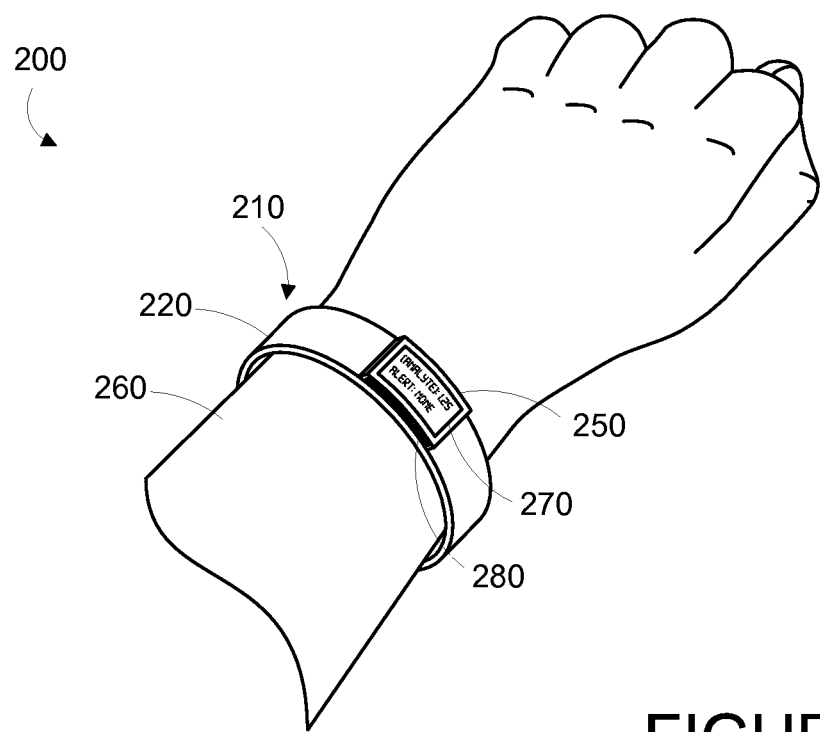
FIG. 2A is a perspective top view of an example wrist-mounted device, when mounted on a wearer's wrist.
Figure 2B:
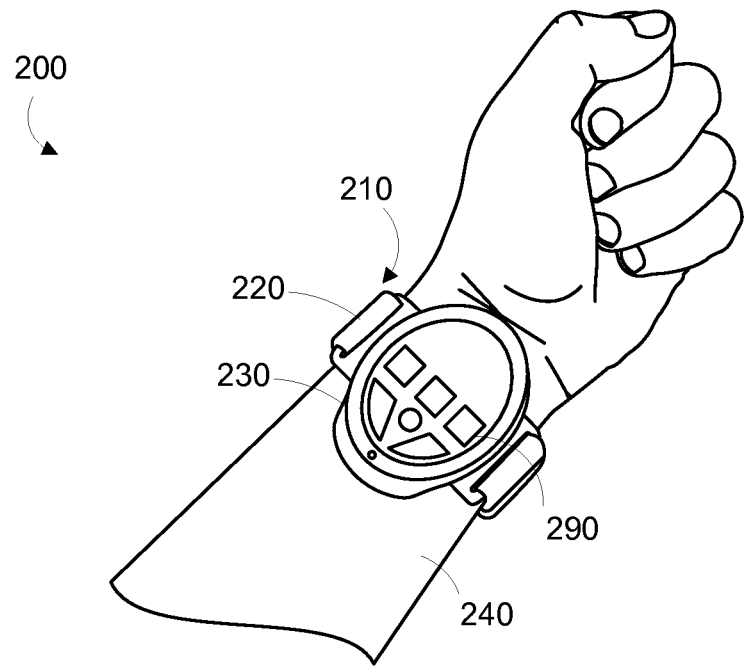
FIG. 2B is a perspective bottom view of an example wrist-mounted device shown in FIG. 2A, when mounted on a wearer's wrist.

In one example, the wearable device is provided as a wrist-mounted device, as shown in FIGS. 2A, 2B, 3A-3C, 4A, 5B, 6 and 7. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
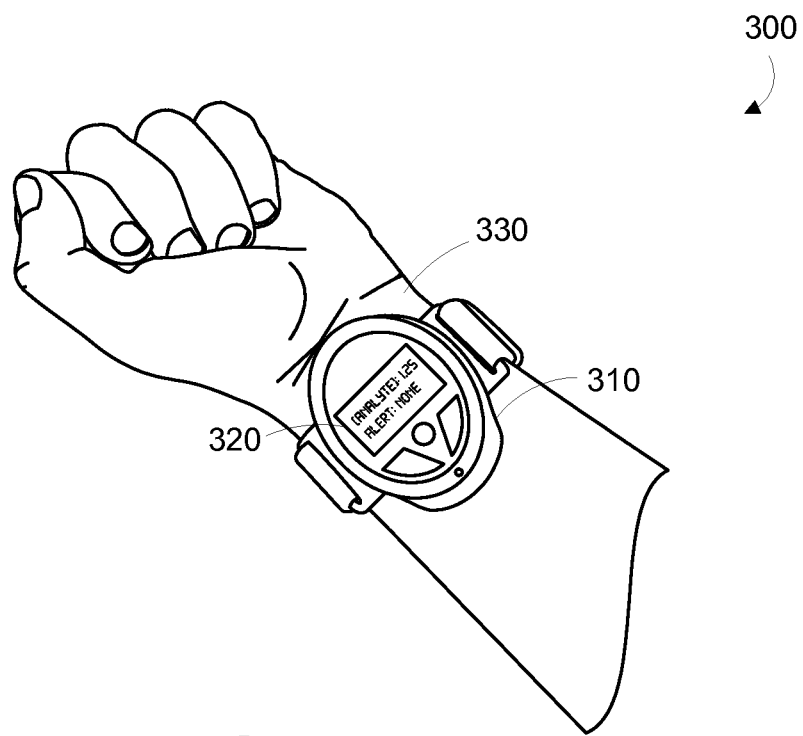
FIG. 3A is a perspective bottom view of an example wrist-mounted device, when mounted on a wearer's wrist.
Figure 3B:
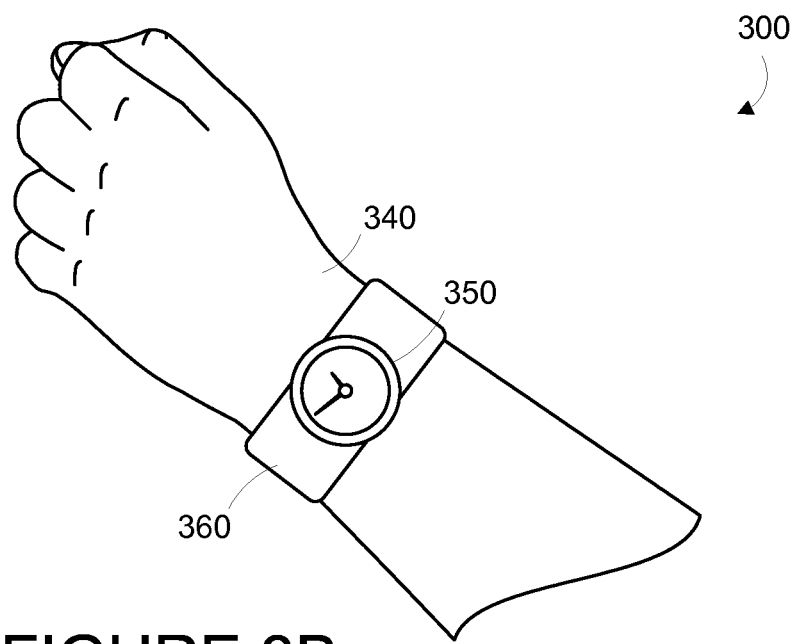
FIG. 3B is a perspective top view of an example wrist-mounted device shown in FIG. 3A, when mounted on a wearer's wrist.
Figure 3C:
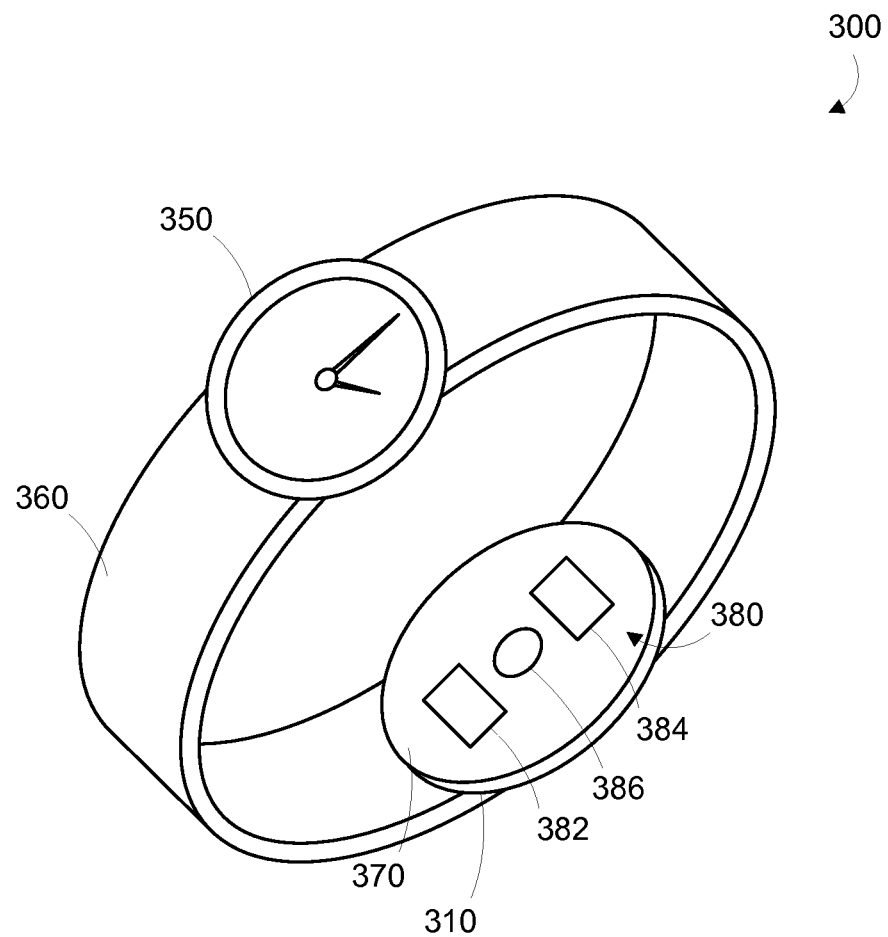
FIG. 3C is a perspective view of an example wrist-mounted device shown in FIGS. 3A and 3B.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
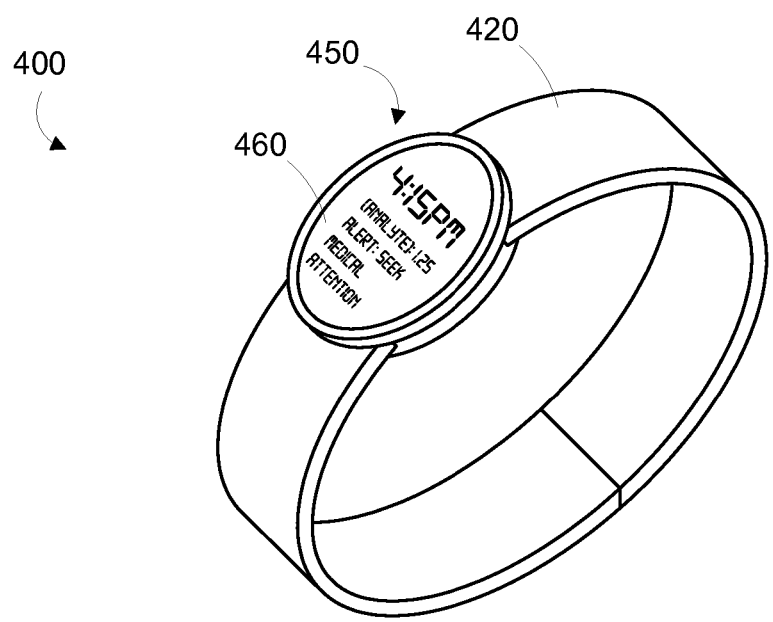
FIG. 4A is a perspective view of an example wrist-mounted device.
Figure 4B:
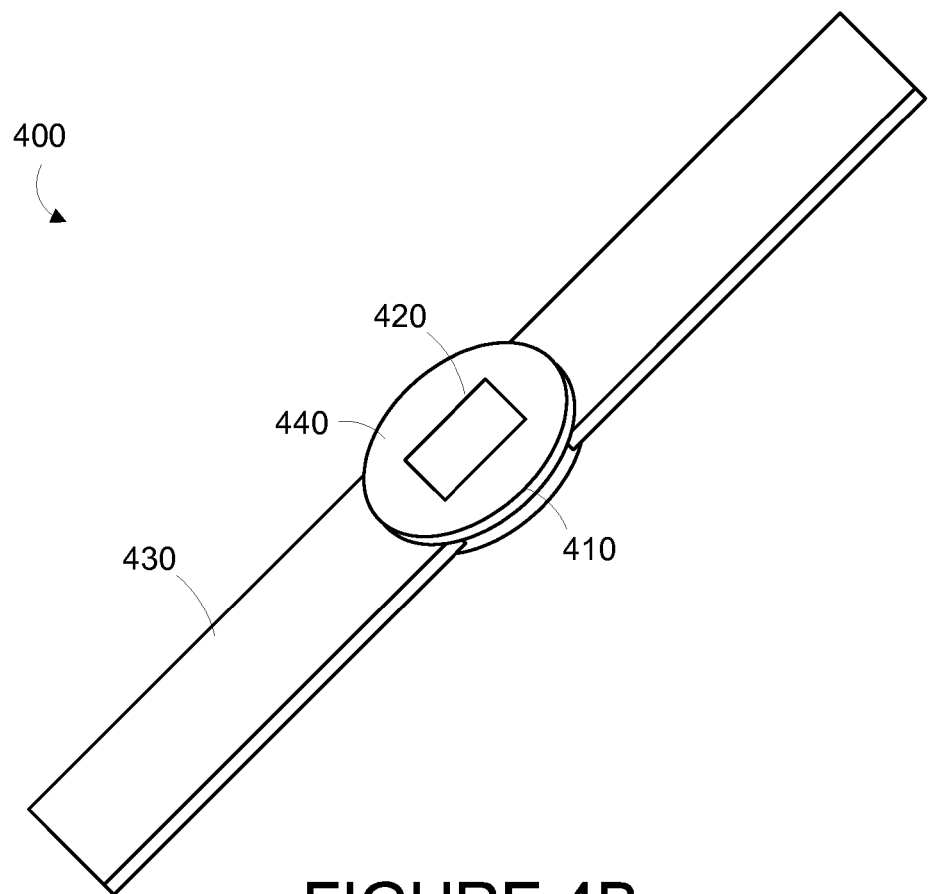
FIG. 4B is a perspective bottom view of an example wrist-mounted device shown in FIG. 4A.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
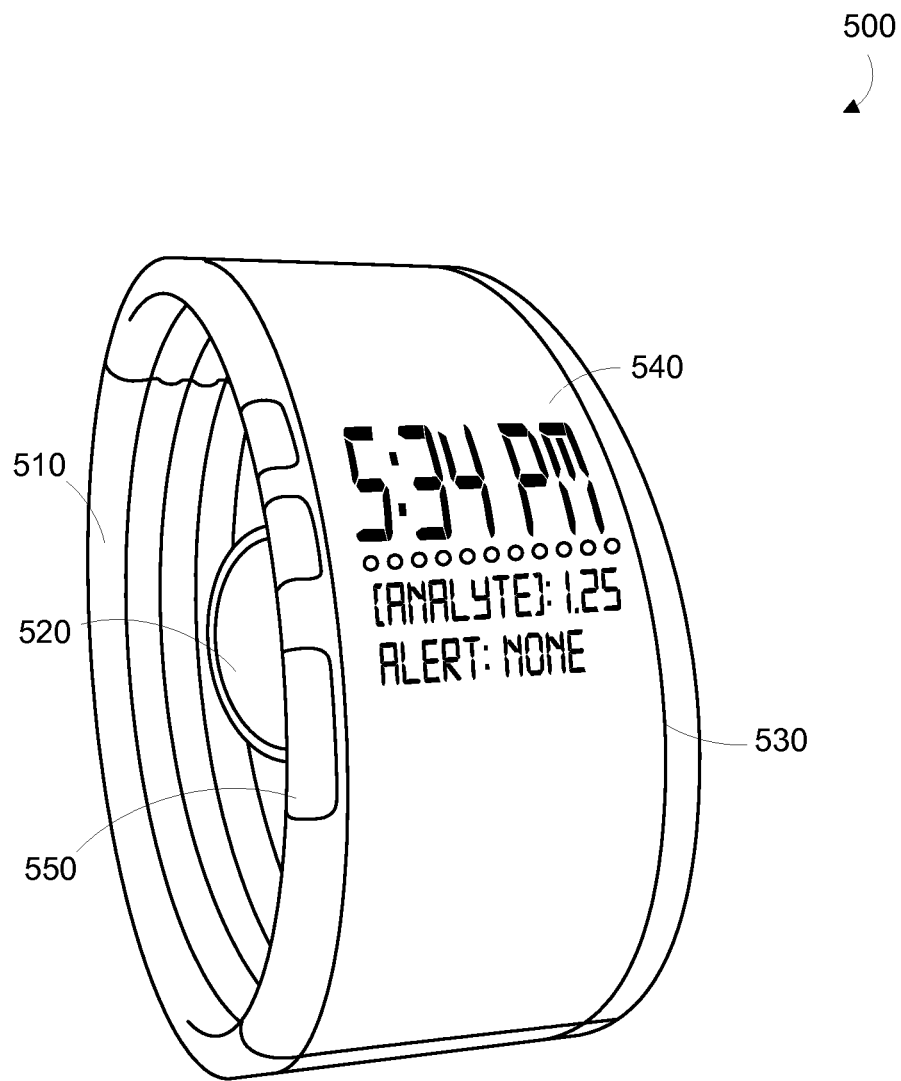
FIG. 5 is a perspective view of an example wrist-mounted device.
Figure 6:
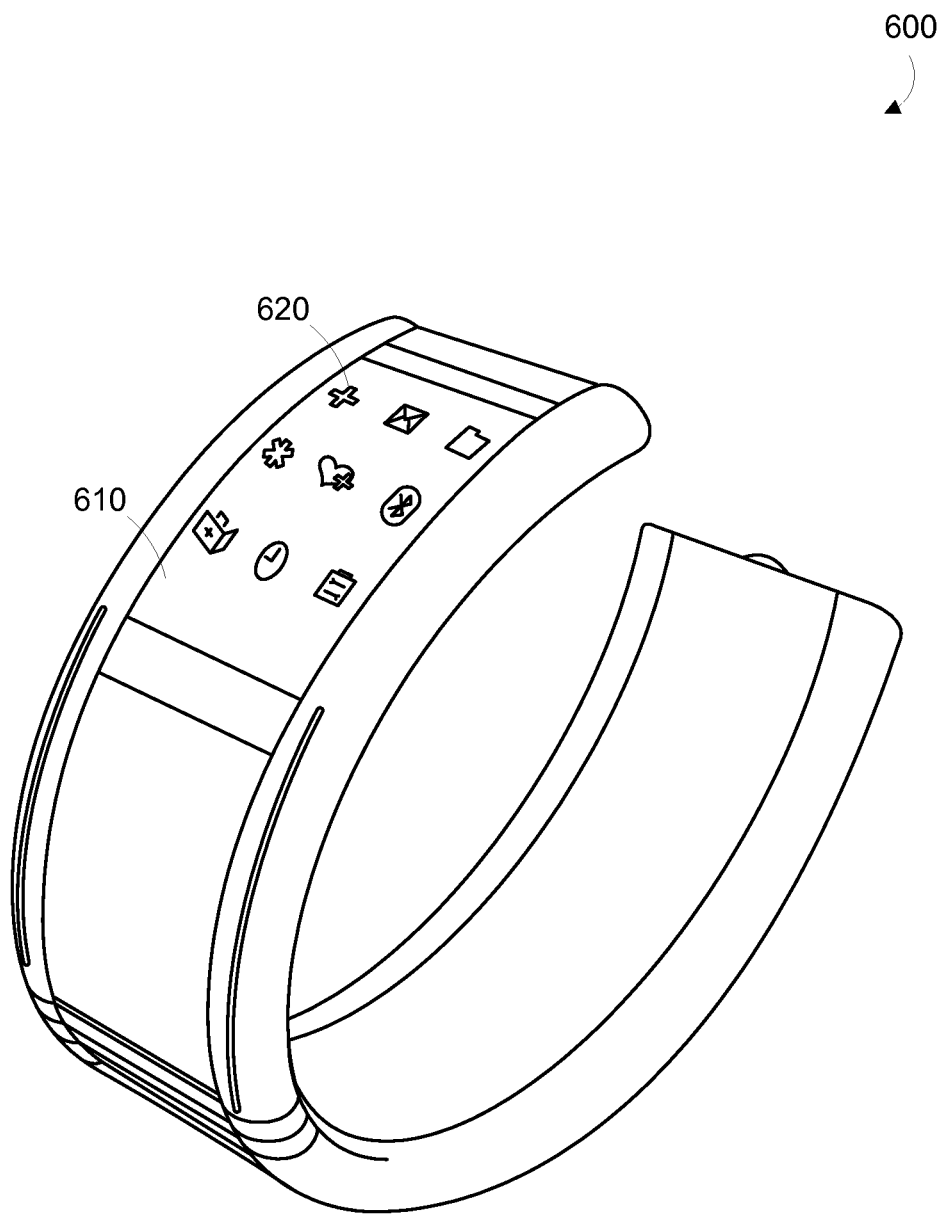
FIG. 6 is a perspective view of an example wrist-mounted device.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health state.

Figure 7:
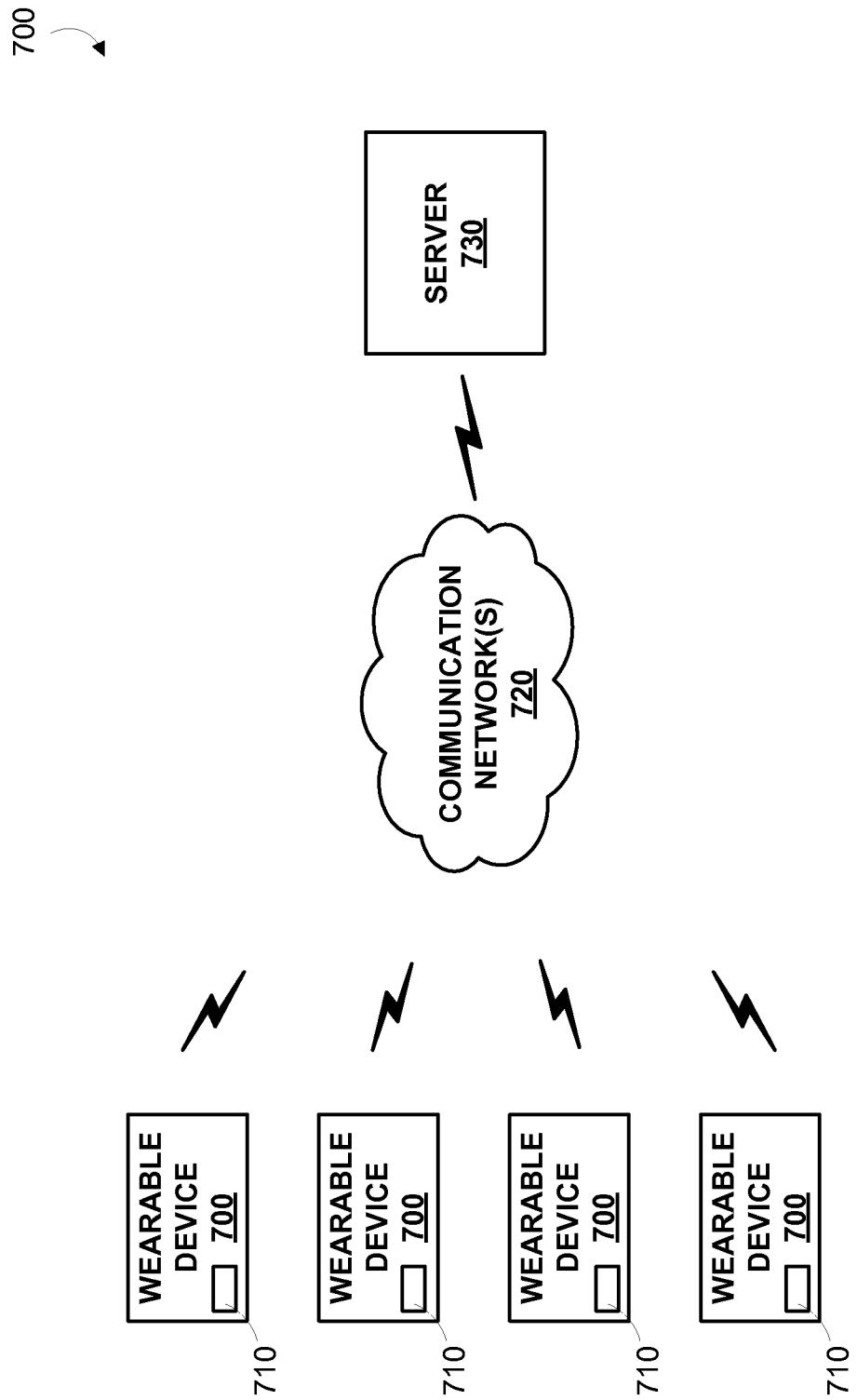
FIG. 7 is a block diagram of an example system that includes a plurality of wearable devices in communication with a server.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Electronics Platform For a Wearable Device

Figure 8:
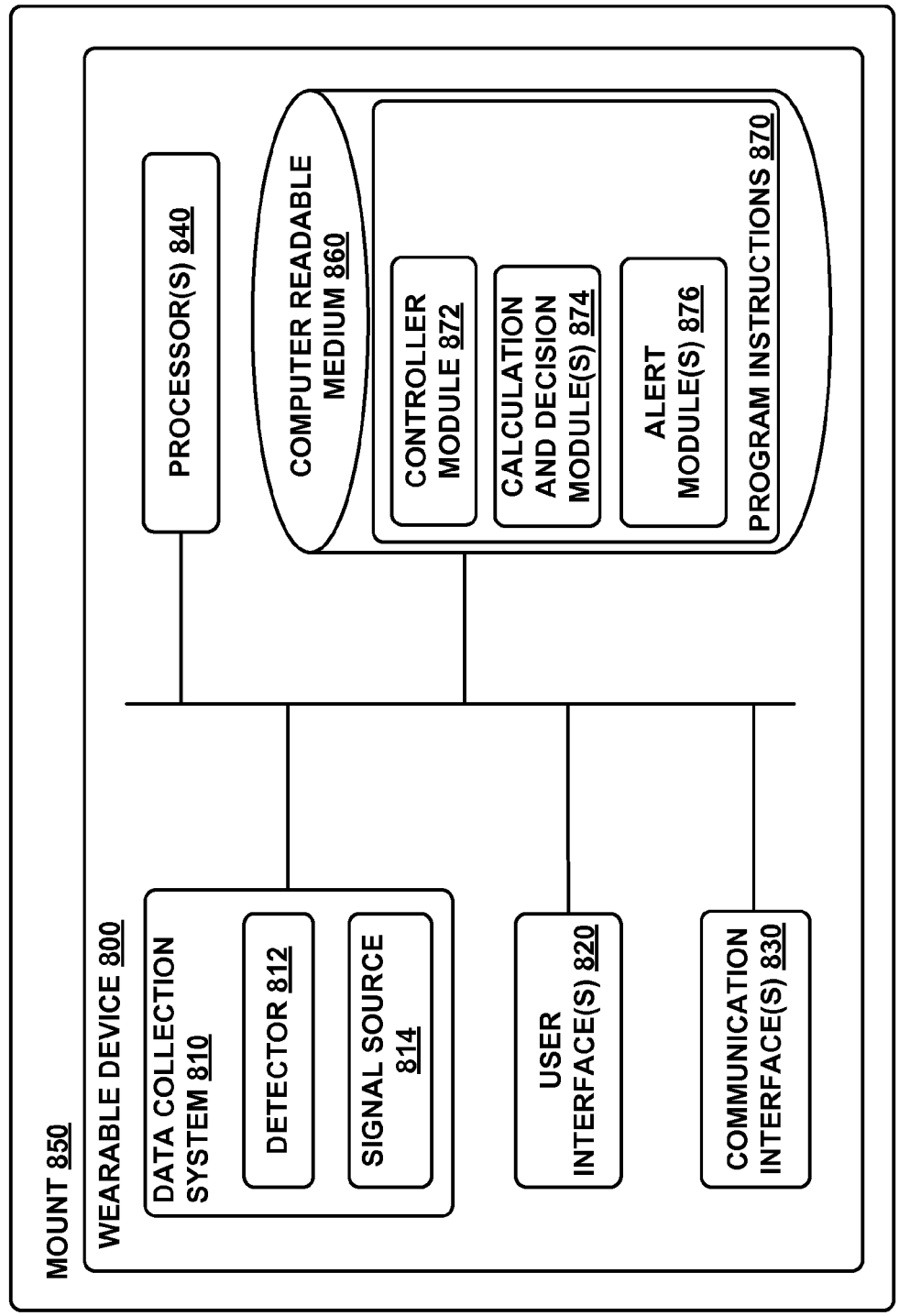
FIG. 8 is a functional block diagram of an example wearable device.

FIG. 8 is a simplified block diagram illustrating the components of a wearable device 800, according to an example embodiment. Wearable device 800 may take the form of or be similar to one of the wrist-mounted devices 200, 300, 400, 500, 600, shown in FIGS. 2A-B, 3A-3C, 4A-4C, 5 and 6. However, wearable device 800 may also take other forms, such as an ankle, waist, or chest-mounted device.

In particular, FIG. 8 shows an example of a wearable device 800 having a data collection system 810, a user interface 820, communication platform 830 for transmitting data to a server, and processor(s) 840. The components of the wearable device 800 may be disposed on a mount 850 for mounting the device to an external body surface where a portion of subsurface vasculature is readily observable.

Processor 840 may be a general-purpose processor or a special purpose processor (e.g., digital signal processors, application specific integrated circuits, etc.). The one or more processors 840 can be configured to execute computer-readable program instructions 870 that are stored in the computer readable medium 860 and are executable to provide the functionality of a wearable device 800 described herein.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes a detector 812 and, in some embodiments, a signal source 814. As described above, detector 812 may include any detector capable of detecting at least one physiological parameter, which could include any parameters that may relate to the health of the person wearing the wearable device. For example, the detector 812 could be configured to measure blood pressure, pulse rate, skin temperature, etc. At least one of the detectors 812 is configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 810 further includes a signal source 814 for transmitting an interrogating signal that can penetrate the wearer's skin into the portion of subsurface vasculature. In general, signal source 814 will generate an interrogation signal that will produce a responsive signal that can be detected by one or more of the detectors 812. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the functionalized particles include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detector 812 and signal source 814. For example, the controller 872 may activate signal source 814 and/or detector 812 during each of the pre-set measurement periods. In particular, the controller module 872 can include instructions for controlling the signal source 814 to transmit an interrogating signal at preset measurement times and controlling the detector 812 to receive data representative of response signals transmitted from the portion of subsurface vasculature in response to the interrogating signals transmitted at the preset measurement times.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication platform 830 may also be operated by instructions within the controller module 872, such as instructions for sending and/or receiving information via a wireless antenna, which may be disposed on or in the wearable device 800. The communication interface 830 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

Calculation and decision module 872 may include instructions for receiving data from the data collection system 810 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 872 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 872 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of the wearer of the device, that may be necessary in determining whether a medical condition is indicated. Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 9:
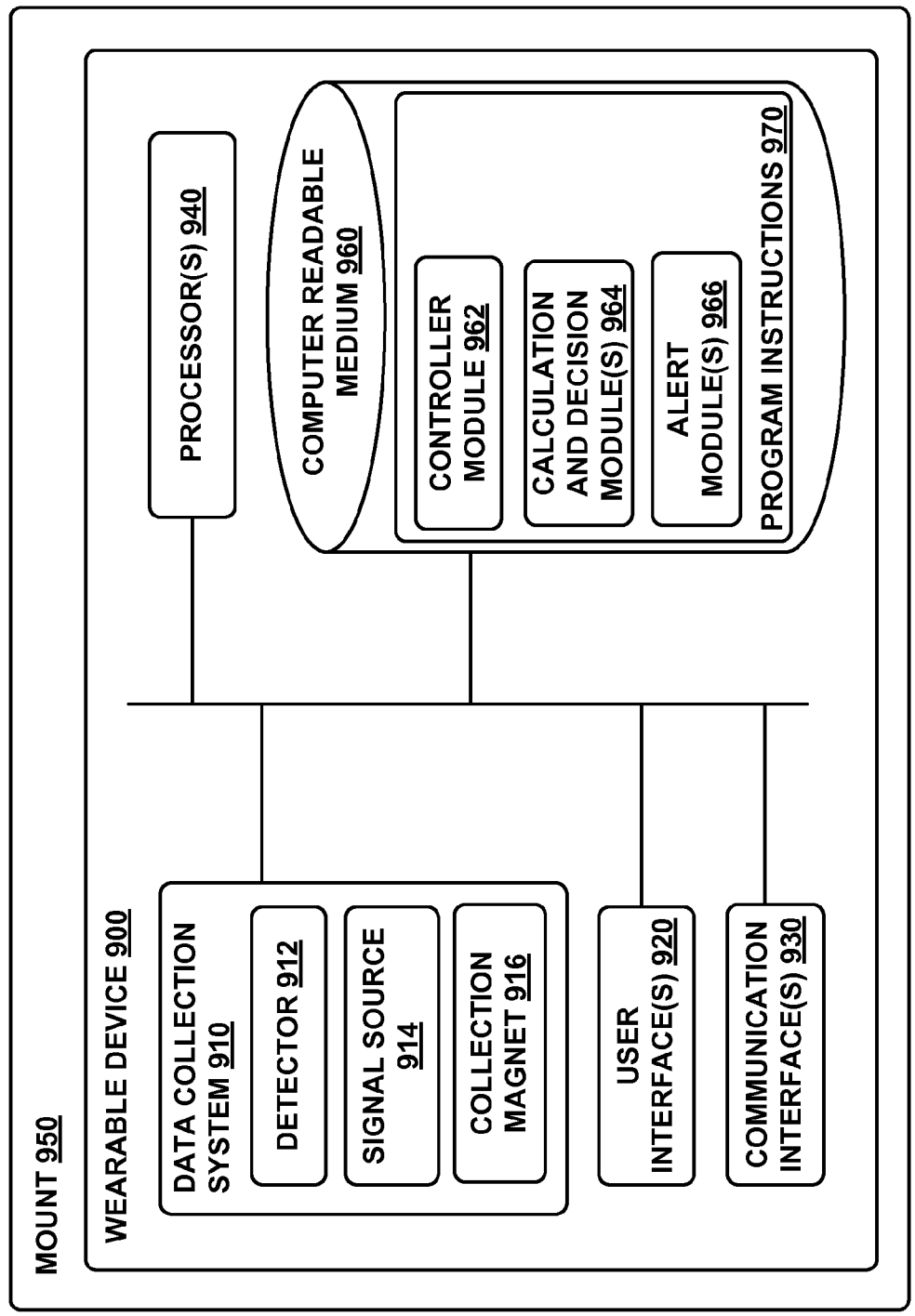
FIG. 9 is a functional block diagram of an example wearable device.

FIG. 9 is a simplified block diagram illustrating the components of a wearable device 900, according to an example embodiment. Wearable device 900 is the same as wearable device 800 in all respects, except that the data collection system 910 of wearable device 900 further includes a collection magnet 916. In this example, the collection magnet 916 may be used to locally collect functionalized magnetic particles present in an area of subsurface vasculature proximate to the collection magnet 916. As described above, collection magnet 916 is configured to direct a magnetic field into a portion of subsurface vasculature sufficient to cause functionalized magnetic particles to collect in a lumen of the portion of subsurface vasculature.

Wearable device 900 includes a data collection system 910, which includes a detector 912, a signal source 914 (if provided) and a collection magnet 916, a user interface 920, a communication interface 930, a processor 940 and a computer readable medium 960 on which program instructions 970 are stored. All of the components of wearable device 900 may be provided on a mount 950. In this example, the program instructions 970 may include a controller module 962, a calculation and decision module 964 and an alert module 966 which, similar to the example set forth in FIG. 8, include instructions to perform or facilitate some or all of the device functionality described herein. Controller module 962 further includes instructions for operating collection magnet 916. For example, controller module 962 may include instructions for activating collection magnet during a measurement period, for a certain amount of time.

IV. Illustrative Functionalized Particles

In some examples, the wearable devices described above obtain at least some of the health-related information by detecting the binding of a clinically-relevant analyte to functionalized particles, for example, microparticles or nanoparticles. The particles can be functionalized by covalently attaching a bioreceptor designed to selectively bind or otherwise recognize a particular clinically-relevant analyte. For example, particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The functionalized particles can be introduced into the person's blood stream by injection, ingestion, inhalation, transdermally, or in some other manner.

The clinically-relevant analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, or other molecule. In one relevant example, certain protein biomarkers are known to be predictive of an impending arterial plaque rupture. Such protein biomarkers are known to be present in the blood only directly leading up to and at the onset of an arterial plaque rupture. Plaques that rupture cause the formation of blood clots that can block blood flow or break off and travel to another part of the body. In either of these cases, if a clot blocks a blood vessel that feeds the heart, it causes a heart attack. If it blocks a blood vessel that feeds the brain, it causes a stroke. If blood supply to the arms or legs is reduced or blocked, it can cause difficulty walking and eventually gangrene. The presence of these protein biomarkers in the vasculature may be detected, and the medical condition (i.e., stroke, heart attack) prevented, by providing particles functionalized with a bioreceptor that will selectively bind to this target analyte.

The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new batches of functionalized particles into the vasculature or body fluids.

Bioreceptors can be used in diagnostic procedures, or even in therapy to destroy a specific target, such as antitumor therapy or targeted chemotherapy. The particles may be designed to remove from the body or destroy the target analyte once bound to the bioreceptor. Additional functional groups may be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, cryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Binding of the functionalized particles to a target analyte may be detected with or without a stimulating signal input. The term "binding" is understood in its broadest sense to include any detectable interaction between the receptor and the target analyte. For example, some particles may be functionalized with compounds or molecules, such as fluorophores or autofluorescent, luminescent or chemiluminescent markers, which generate a responsive signal when the particles bind to the target analyte without the input of a stimulus. In other examples, the functionalized particles may produce a different responsive signal in their bound versus unbound state in response to an external stimulus, such as an electromagnetic, acoustic, optical, or mechanical energy.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period. Such collection may not only increase the differential velocity between particles and analytes, hence surveying a much larger volume per unit time, but may also enhance the signal for subsequent detection.

V. Illustrative Methods For Operation of a Wearable Device

Figure 10:
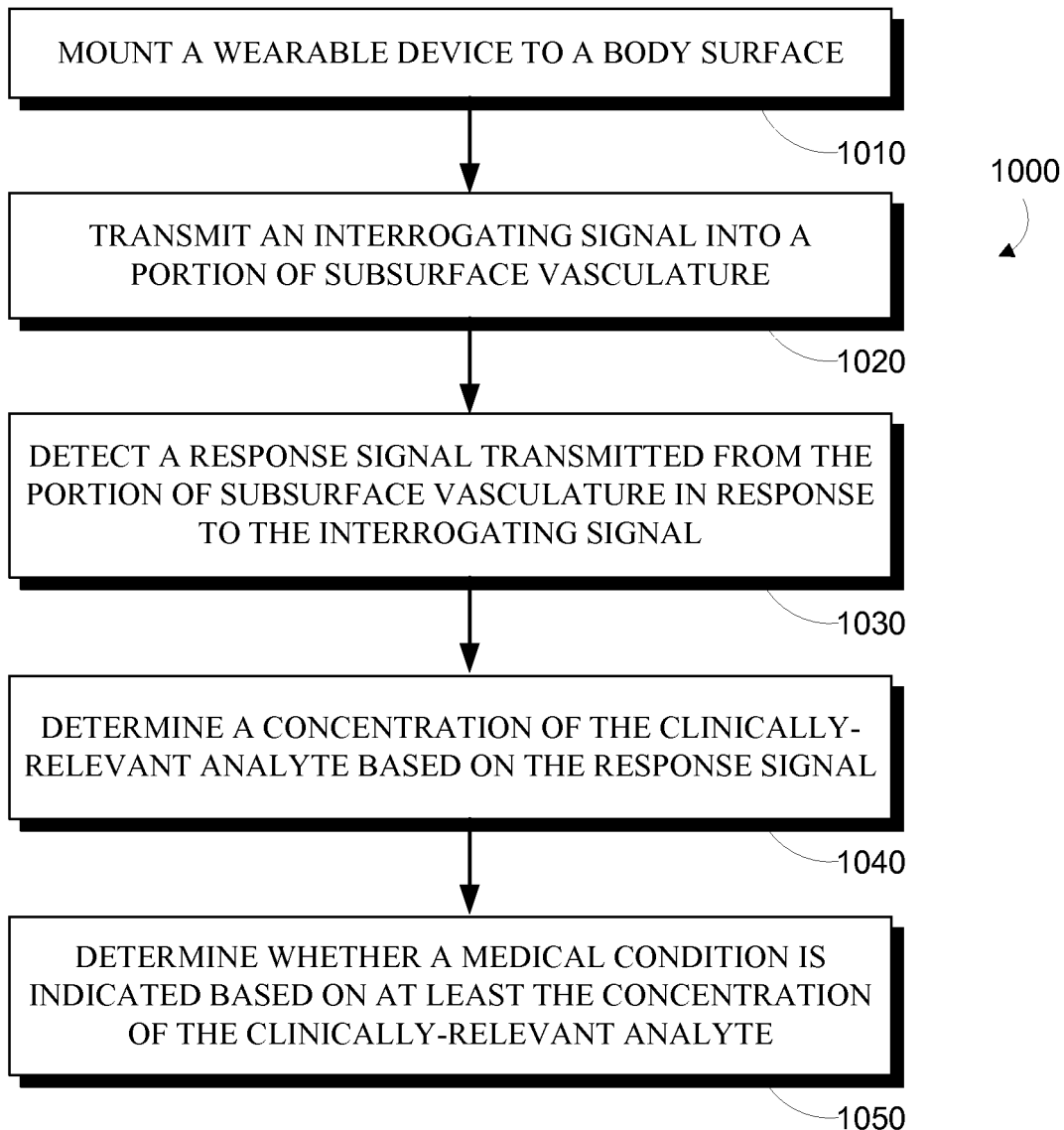
FIG. 10 is a flowchart of an example method for operating a wearable device.

FIG. 10 is a flowchart of a method 1000 for operating a wearable device to take non-invasive, in vivo, real-time measurements of physiological parameters. A wearable device is first mounted to a body surface of a human subject, wherein the body surface is proximate to a portion of subsurface vasculature (1010). In some examples, the wearable device, via a signal source, transmits an interrogating signal into the portion of subsurface vasculature (1020). The wearable device, via a detector, then detects a response signal transmitted from the portion of subsurface vasculature, wherein the response signal is related to binding of a clinically-relevant analyte to functionalized particles present in a lumen of the subsurface vasculature (1030). In some examples, the response signal is generated in response to an interrogating signal. The functionalized particles are configured to bind to the clinically-relevant analyte and may comprise a receptor, such as an antibody. The term "bind" is understood in its broadest sense to also include any detectable interaction between the clinically relevant analyte and the functionalized particles. The wearable device then determines the presence, absence and/or a concentration of the clinically-relevant analyte based on the response signal (1040) and whether a medical condition is indicated based on at least the presence, absence and/or concentration of the clinically-relevant analyte (1040). Further, in examples where the functionalized particles are magnetic, the wearable device may further direct a magnetic field into the portion of subsurface vasculature, the magnetic field being sufficient to cause the functionalized magnetic particles to collect in a lumen of the portion of subsurface vasculature.

FIGS. 11A-11B, 12A-12B, and 13A-13B are partial cross-sectional side views of a human wrist illustrating the operation of various examples of a wrist-mounted device. In the example shown in FIGS. 11A and 11B, the wrist-mounted device 1100 includes a measurement platform 1110 mounted on a strap or wrist-band 1120 and oriented on the anterior side 1190 of the wearer's wrist. Measurement platform 1110 is positioned over a portion of the wrist where subsurface vasculature 1130 is easily observable. Functionalized particles 1140 have been introduced into a lumen of the subsurface vasculature by one of the means discussed above. In this example, measurement platform 1110 includes a data collection system having both a detector 1150 and a signal source 1160. FIG. 11A illustrates the state of the subsurface vasculature when measurement device 1100 is inactive. The state of the subsurface vasculature during a measurement period is illustrated in FIG. 11B. At this time, signal source 1160 is transmitting an interrogating signal 1162 into the portion of subsurface vasculature and detector 1150 is receiving a response signal 1152 generated in response to the interrogating signal 1162. The response signal 1152 is related to the binding of a clinically relevant analyte present in the subsurface vasculature to the functionalized particles 1140. As described above, in some embodiments, an interrogating signal may not be necessary to generate a response signal related to the binding of an analyte to the functionalized particles.

Similar to the system depicted in FIGS. 11A and 11B, FIGS. 12A and 12B illustrate a wrist-mounted device 1200 including a measurement platform 1210 mounted on a strap or wristband 1220 and oriented on the anterior side 1290 of the wearer's wrist. In this example, measurement platform 1210 includes a data collection system having a detector 1250, a signal source 1260 and a collection magnet 1270. FIG. 12A illustrates the state of the subsurface vasculature when measurement device 1200 is inactive. The state of the subsurface vasculature when measurement device 1200 is active during a measurement period is illustrated in FIG. 12B. At this time, collection magnet 1270 generates a magnetic field 1272 sufficient to cause functionalized magnetic particles 1240 present in a lumen of the subsurface vasculature 1230 to collection in a region proximal to the magnet 1270. Signal source 1260 transmits an interrogating signal 1262 into the portion of subsurface vasculature and detector 1250 is receiving a response signal 1252 generated in response to the interrogating signal 1262. The response signal 1252 is related to the binding of a clinically relevant analyte present in the subsurface vasculature to the functionalized magnetic particles 1240. As described above, in some embodiments, an interrogating signal may not be necessary to generate a response signal related to the binding of an analyte to the functionalized magnetic particles.

Figure 13A:
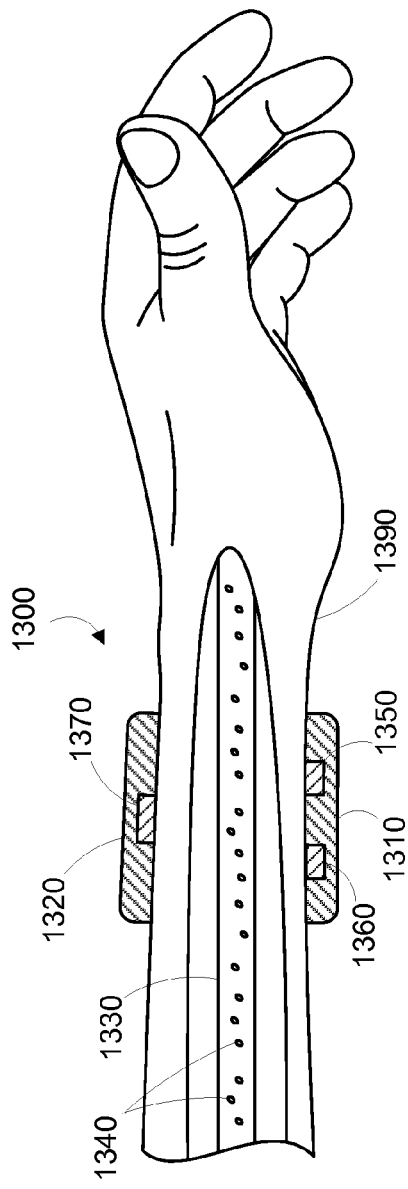
FIG. 13A is side partial cross-sectional view of a wrist-mounted device, while on a human wrist.
Figure 13B:
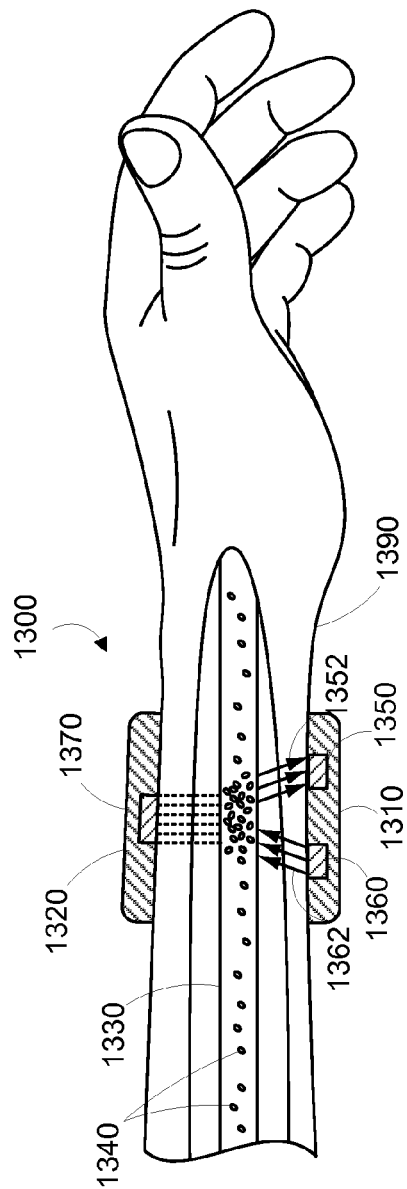
FIG. 13B is side partial cross-sectional view of a wrist-mounted device, while on a human wrist.

FIGS. 13A and 13B illustrate a further embodiment of a wrist-mounted device 1300 having a measurement platform 1310 disposed on a strap 1320, wherein the detector 1350 and signal source 1360 are positioned on the posterior side 1390 of the wearer's wrist and the collection magnet 1370 is disposed on the anterior side 1380 of the wearer's wrist. Similar to the embodiments discussed above, FIG. 13A illustrates the state of the subsurface vasculature when measurement device 1300 is inactive. The state of the subsurface vasculature when measurement device 1300 is active during a measurement period is illustrated in FIG. 13B. At this time, collection magnet 1370 generates a magnetic field 1232 sufficient to cause functionalized magnetic particles 1340 present in a lumen of the subsurface vasculature 1330 to collection in a region proximal to the magnet 1370. Signal source 1360 transmits an interrogating signal 1362 into the portion of subsurface vasculature and detector 1350 is receiving a response signal 1352 generated in response to the interrogating signal 1262. The response signal 1352 is related to the binding of a clinically relevant analyte present in the subsurface vasculature to the functionalized magnetic particles 1340. As described above, in some embodiments, an interrogating signal may not be necessary to generate a response signal related to the binding of an analyte to the functionalized magnetic particles.

Both FIGS. 12B and 13B illustrate the path of the interrogating signal (1262, 1362) transmitted by the signal source (1260, 1360) and the responsive signal (1252, 1352) detected by the detector (1250, 1350) essentially overlapping over a portion of subsurface vasculature. In some examples, the signal source (1260, 1360) and the detector (1250, 1350) may be angled towards each other so that they are interrogating and detecting from essentially the same area of subsurface vasculature. However, in some instances, such as in the example shown in FIG. 11B, the paths of the interrogating signal (1262, 1362) transmitted by the signal source (1260, 1360) and the responsive signal (1252, 1352) detected by the detector (1250, 1350) may not overlap.

Figure 14:
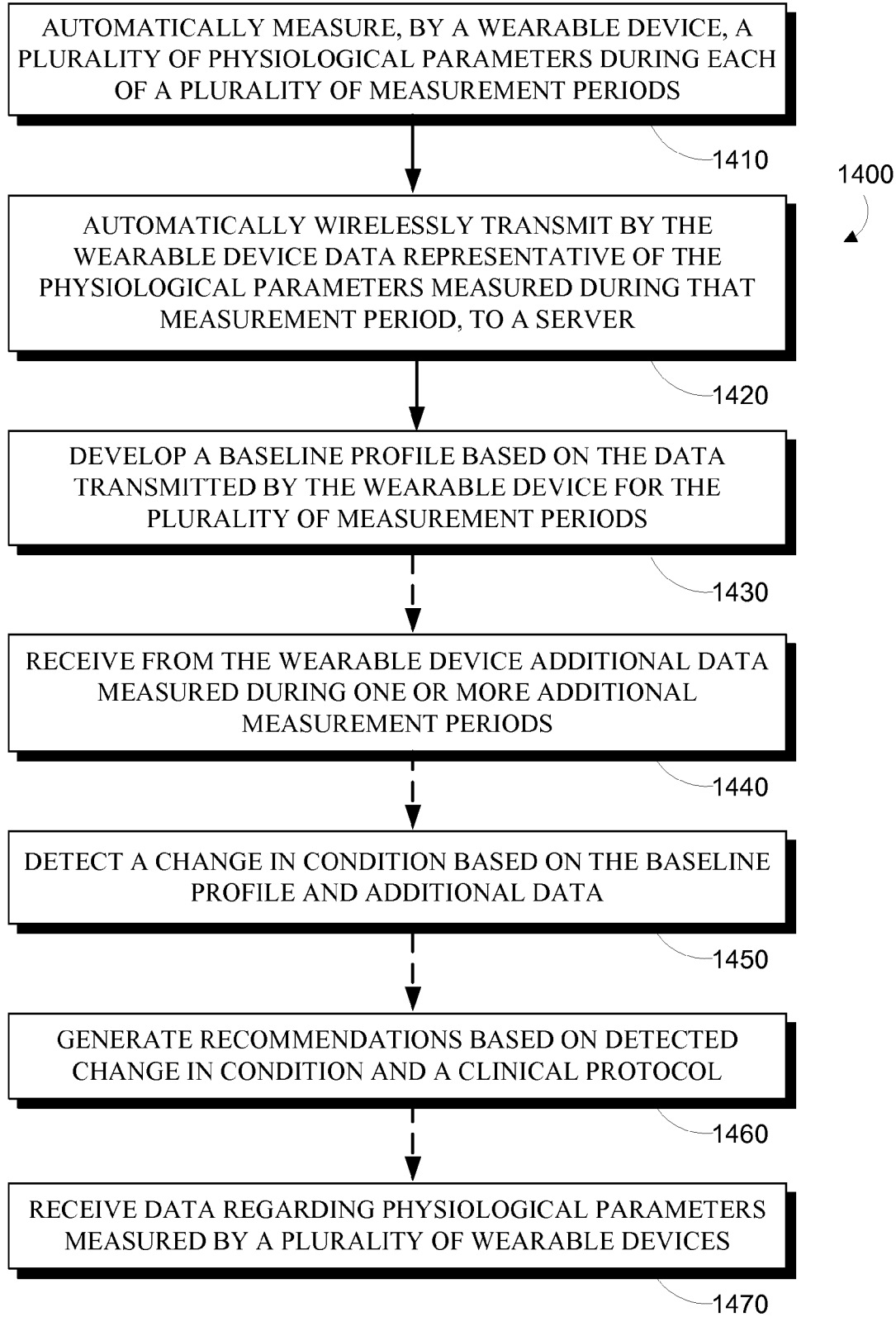
FIG. 14 is a flowchart of an example method for using a wearable device to take real-time, high-density, non-invasive, in vivo measurements of physiological parameters.

VI. Illustrative Methods For Real-Time, High-Density Physiological Data Collection Using a Wrist Mounted Device FIG. 14 is a flowchart of a method 1400 for using a wearable device to take real-time, high-density, non-invasive, in vivo measurements of physiological parameters. In a first step, the wearable device automatically measures one or more physiological parameters during each of a plurality of measurement periods (1410). The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server data representative of the physiological parameters measured during that measurement period (1420). The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server is configured to develop a baseline profile based on the data transmitted by the wearable device for the plurality of measurement periods (1430). In some embodiments, the baseline profile includes an individual baseline profile based on the data transmitted by the wearable device for the plurality of measurement periods for an individual user wearing the wearable device. As described above, the baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the server may receive additional data regarding the physiological parameters from the wearable device measured during one or more additional measurement periods (1440). The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition (1450). The change in condition could, for example, indicate that the wearer has developed a disease, disorder, or other adverse medical condition or may be at risk for a severe medical condition, such as a stroke or a heart attack, in the near future.

If the server detects a change in condition based on the individual baseline profile and the additional data, it may generate one or more recommendations based on the detected change in condition and a clinical protocol (1460). For example, the server may generate a recommendation that the wearer take a particular medication or supplement, schedule an appointment with a medical professional, go to the hospital to seek immediate medical attention, abstain from certain activities, etc. The server may also be configured to receive data regarding physiological parameters measured by a plurality of wearable devices (1470) and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server (1470) and providing an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

Figure 15:
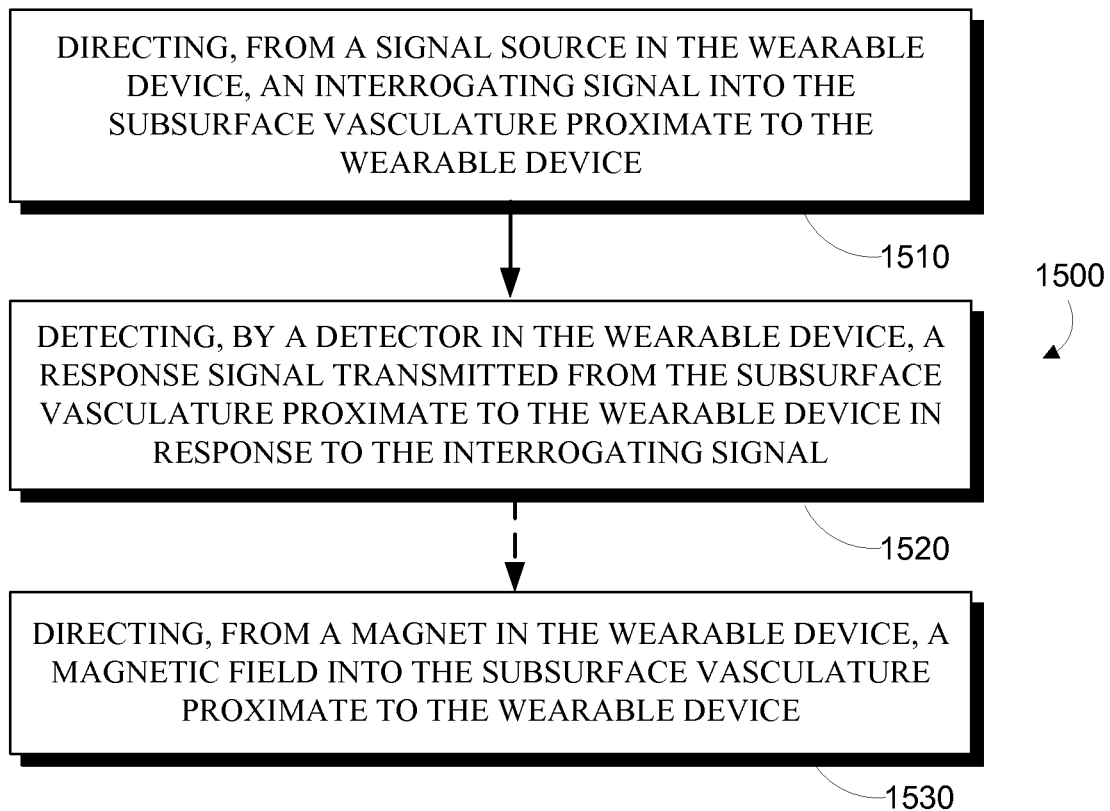
FIG. 15 is a flowchart of an example method for using a wearable device to take real-time, high-density, non-invasive, in vivo measurements of physiological parameters, in particular steps for measuring one or more analytes in blood circulating in subsurface vasculature proximate to the wearable device.

In further embodiments, the method may include introducing functionalized particles into the blood, wherein the functionalized magnetic particles are configured to bind to the one or more analytes. As shown in FIG. 15, the wearable device may non-invasively measure one or more analytes in blood circulating in subsurface vasculature proximate to the wearable device by directing, from a signal source in the wearable device, an interrogating signal into the subsurface vasculature proximate to the wearable device (1510). As discussed above, this step may not be necessary in cases where the functionalized particles generate a response signal related to binding of the one or more analytes without the need for an interrogating signal. In any case, the wearable device may detect, with a detector, a response signal transmitted from the subsurface vasculature proximate to the wearable device in response to the interrogating signal (1520). The response signal is related to binding of the one or more analytes to the functionalized particles. In examples where an interrogating signal is used, the interrogating signal may include a time-varying magnetic field and the response signal may include an externally-detectable physical motion due to the time-varying magnetic field. The interrogating signal may include an electromagnetic pulse (e.g., a radio frequency (RF) pulse) and the response signal may include a magnetic resonance (MR) signal. The interrogating signal may include electromagnetic radiation having a wavelength between about 400 nanometers and about 1600 nanometers, more particularly, a wavelength between about 500 nanometers and about 1000 nanometers. Where the functionalized particles also include a fluorophore, the response signal may include fluorescence radiation transmitted by the fluorophore in response to the interrogating signal.

In some examples, the functionalized particles may also be magnetic. The process of measuring one or more analytes in blood circulating in subsurface vasculature may further include directing, from a magnet in the wearable device, a magnetic field into the subsurface vasculature proximate to the wearable device (1530). The magnetic field is sufficient to cause the functionalized magnetic particles to collect in a lumen of the subsurface vasculature proximate to the wearable device.

Figure 16:
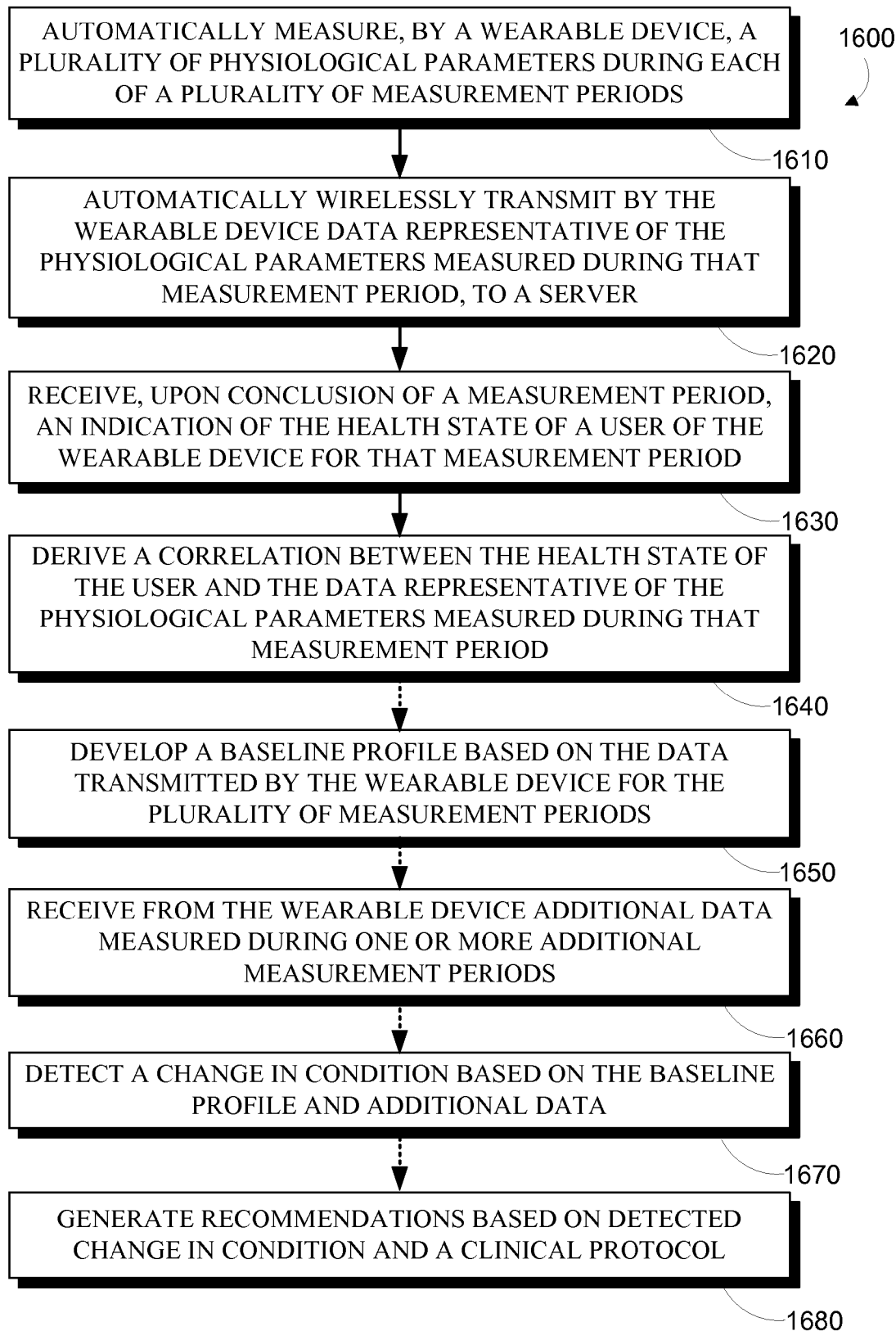
FIG. 16 is a flowchart of an example method for using a wearable device to take real-time, high-density, non-invasive, in vivo measurements of physiological parameters.

FIG. 16 is a flowchart of a method 1600 for using a wearable device to take real-time, high-density, non-invasive, in vivo measurements of physiological parameters. In a first step, the wearable device automatically measures one or more physiological parameters during each of a plurality of measurement periods (1610). The measurement periods may extend through a plurality of consecutive days, wherein each of the consecutive days includes multiple measurement periods. At least some of the physiological parameters are measured by non-invasively detecting one or more analytes in blood circulating in subsurface vasculature proximate to the wearable device.

Upon conclusion of a measurement period for each of the plurality of measurement periods, the wearable device automatically wirelessly transmits to a server data representative of the physiological parameters measured during that measurement period (1620). The server may be configured to receive, upon conclusion of a measurement period, an indication of the health state of a user of the wearable device for that measurement period and derive a correlation between the health state of the user and the data representative of the physiological parameters measured during that measurement period (1630). For example, the server may be configured to recognize patterns, for example, every time a physiological parameter reaches or drops to a certain level, the wearer of the device indicates that he or she experiences a migraine. Recognition of these patterns or correlations may help medical professionals to recognize, prevent, diagnose and/or treat of health conditions in that individual. Further, the server may be configured to use these correlation to alert the user that a medical condition may be imminent.

A baseline profile may be developed by the server based on the data transmitted by the wearable device for the plurality of measurement periods (1650). The server may further be configured to receive from the wearable device additional data representative of the physiological parameters measured during one or more additional measurement periods (1660), detect a change in condition based on the baseline profile and the additional data (1670), and generate one or more recommendations based on the detected change in condition and a clinical protocol (1680). The clinical protocol may be developed based, at least in part, on the derived correlation. For example, the clinical protocol may indicate that a medical condition may be imminent based on a comparison between current measurement of a physiological parameter and the derived correlation between previously measured physiological parameters and previously reported health state.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

VII. Illustrative Non-invasive Analyte Detection System With Modulation Source The signal-to-noise ratio (SNR) in an analyte detection system, such as any of those described above, may be increased by modulating the analyte response signal transmitted from the subsurface vasculature (or other body system) with respect to the background signal and, in some cases, an unbound particle response signal. Such modulation can increase the system's sensitivity and ability to discern between target analytes present in the blood or other bodily fluids, versus other analytes, particles, cells, molecules, blood components, bone and tissues, etc. This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

FIGS. 17A-17B, which are partial cross-sectional side views of a human wrist, illustrate the operation of an example system 1700 including functionalized particles 1740 configured to interact with one or more target analytes present in blood or other bodily fluid, a detector 1750 configured to detect a response signal 1752 transmitted form a portion of the body, such as the subsurface vasculature, and a modulation source 1770 configured to modulate the response signal 1752. The functionalized particles 1740 may be introduced into the body, for example, into a lumen of the subsurface vasculature 1730 by any known route, including orally, transdermally, topically, transmucosally, intramuscularly, etc. In some embodiments, the system 1700 may also include a signal source 1760, but as described above, an interrogating signal 1762 is not necessary in every case to generate a response signal 1752. Further, in some embodiments, the signal source 1760 itself may be modulated (thereby modulating the response signal 1752 as well). In these embodiments, the modulation and interrogation are essentially combined.

In some embodiments, the system 1700 may be implemented with a wearable device 1710, which may include any device that is capable of being worn at, on or in proximity to a body surface, such as a wrist, ankle, waist, chest, or other body part. The wearable device 1710 may be positioned on or in proximity to a portion of the body where subsurface vasculature 1730 (or other body system) is readily observable, so that analyte measurements may be taken noninvasively from outside of the body. The device 1710 may be placed in close proximity to the skin or tissue, but need not be touching or in intimate contact therewith. Additionally or alternatively, the system 1700 may be implemented by implanting one or more of the components, such as the detector 1750, signal source 1760 and/or modulation source 1770 under the skin, at a position where the subsurface vasculature, or other body system, is readily observable. System 1700 may also be implemented as a stationary device or as a device which may be temporarily held against or in proximity to a body surface for one or more measurement periods.

A mount 1720, such as a belt, wristband, wristwatch, ankle band, headband, eyeglasses, necklace, earrings, etc. can be provided to mount or stabilize the device 1710 at, on or in proximity to a body surface. The mount 1720 may prevent the wearable device 1710 from moving relative to the body to reduce measurement error and noise. Further, the mount 1720 may be an adhesive substrate for adhering the wearable device to the body of a wearer. The detector 1750, modulation source 1770, interrogation signal source 1760 (if applicable) and, in some examples, a processor (not shown), or portions thereof may be provided on the wearable device 1710. Mount 1720 may be designed such that device 1710 may be worn continuously without interfering with the wearer's daily activities so that measurements may be taken throughout the day. In other examples, the mount 1720 may be designed to temporarily hold the device 1710 on or near the body during measurement periods only. Each of the detector 1750, modulation source 1770 and signal source 1760 (if applicable) can be located proximal to one another on the same portion of the mount as shown in FIGS. 17A-17B, or can be positioned at different locations on the mount 1720.

The state of the subsurface vasculature during a measurement period is illustrated in FIG. 17B. In this embodiment, signal source 1760 transmits an interrogating signal 1762 into a portion of the body and detector 1750 receives a response signal 1752 transmitted from the body. The response signal 1752 may include an analyte response signal, an unbound particle signal and a background signal. The analyte response signal is related to the interaction of a target analyte present in the body with the functionalized particles 1740 and may, in some cases, be generated in response to an interrogating signal 1762. As described above, in some embodiments, an interrogating signal may not be necessary to generate a response signal related to the binding of an analyte to the functionalized particles. Further, in other examples, the modulation source may essentially act as a signal source by generating a modulated interrogation signal.

The modulation source 1770 applies a modulation 1772, configured to modulate the response signal, to the portion of the body. Specifically, the modulation source 1770 may be configured to modulate the analyte response signal differently from a background signal. The background signal may include any signal transmitted from something other than what the system 1700 is monitoring, i.e., the target analyte (s). In some examples, the background signal may be generated by other molecules, cells, or particles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

Both bound particles 1742 and unbound particles 1744 may be present in the subsurface vasculature 1730 in the area of the wearable device 1710. "Bound" particles 1742 include any particles that are bound to or otherwise interacting with the target analyte(s). The analyte response signal is transmitted from these bound particles 1742. Conversely, "unbound" particles 1744 include any particles that are not bound to or otherwise interacting with the target analyte(s). The unbound particles 1744 may produce an unbound particle signal (not shown) that is not related to the binding or interaction of the target analyte(s) with the functionalized particles 1740. In some examples, the modulation source 1770 may be configured to modulate the analyte response signal differently than the unbound particle signal, such that the analyte response signal may be differentiated from the unbound particle signal. Such differentiation may be used to determine the number or percentage of particles 1740 bound to or interacting with the target analyte(s), which may be used to determine a concentration of the target analyte(s) in the blood or other bodily fluid, to determine if and to what extent the particles are being cleared from the body, etc.

The modulation source 1770 may include any means for modulating the response signal 1752. In some cases, the analyte response signal may be modulated differently than the background signal, and in other cases the analyte response signal may be modulated differently than the unbound particle signal, or both. For example, the modulation source 1770 may be configured to alter the analyte response signal by spatially modulating the bound particles 1742. The modulation source 1770 may be configured to modulate the optical properties, including the fluorescence, luminescence or chemiluminescence of the bound particles 1742. In further examples, the modulation source 1770 may be configured to alter the magnetic, electric, acoustic, and/or physical properties of the bound particles 1742. The modulation source 1770 may be a physical construct or it may be a signal or energy applied to the body, or a combination thereof. Accordingly, the modulation 1772 may include spatial, temporal, spectral, thermal, magnetic, optical, mechanical, electrical, acoustic, chemical, or electrochemical type of modulation or any combination thereof.

In one example, the modulation source 1770 may be configured to spatially modulate the analyte response signal. For example, a spatial modulation may exploit the speed, rotation, size, thermodynamic properties, hydrodynamic properties, etc. of the bound particles, versus unbound particles and other items that are not of interest, travelling within the vasculature 1730 to distinguish the analyte response signal. For example, an analyte-bound particle is going to have a different size and shape than an unbound particle and, therefore, may travel through the subsurface vasculature a different speed, thereby modulating between bound and unbound particles. In one example, analyte-bound magnetic particles may travel through the subsurface vasculature at a different speed when subject to a magnetic field than unbound magnetic particles. The modulation source 1770 may be used to exploit this difference in speed to differentiate the analyte response signal from other signals transmitted from the body.

Other forces, such as magnetic or acoustic forces, may be used to influence the spatial properties or motion of the particles through the vasculature, thereby further distinguishing between particles with different hydrodynamic properties in the blood flow (e.g. large vs., small, bound vs. unbound, shapes, buoyancy and the like). For example, magnetic particles will align and orient themselves in a static magnetic field, but Brownian motion will randomize their angular positions when the magnetic field is removed. The rate of randomization may depend on the size and shape of the particle, i.e. on whether it is bound to another object or not. Similarly, the rotational or translational response of a particle to a time varying magnetic field may also depend on the size, shape and hence binding state of the particle. The size, shape or binding state dependency may manifest itself as a variation in motion amplitude, as a variation in frequency response, as a phase shift or combinations thereof. Other motive forces, such as acoustic forces for example, are also possible.

In general, spatial-modulation techniques may rely on observing the spatial response of particles when subjected to motive forces (magnetic, acoustic or other) in a hydrodynamic drag medium (e.g., blood). Both the motive force and the hydrodynamic drag force may be dependent on size, shape or binding state of the particle. Further, these techniques may allow for measurement of the size/shape of the particle or the size of the object the particle is bound to. Exploitation of the motive differences may also allow for bound particles to be spatially separated from unbound particles, or small particles from larger particles, or round particles from oblong particles etc. Spatial separation improves the signal to noise ratio for detecting particle properties and binding state.

In another example, the modulation 1772 may be based on the direct modulation of nanodiamond particles. Nanodiamonds are substances having nitrogen point defects that will fluoresce in the near-IR range. The intensity of the nanodiamond fluorescence can be influenced by a magnetic field—the higher the magnetic field, the lower the fluorescence. Accordingly, by exposing the nanodiamonds to a pulsed magnetic field, the intensity of fluorescence can be modulated. Radio frequency (RF) energy can also influence the intensity of fluorescence.

Thermal modulation may also be employed in some examples. Thermal energy may be used to cause a change a number of other particle characteristics that may be useful in modulating the analyte response signal, such as, fluorescence wavelength, fluorescence intensity, acoustic emission frequency or amplitude, or particle confirmation. These characteristic changes may be used to differentiate the bound particles from unbound particles and from background noise. In one example, an energy absorbing particle may be irradiated with pulsed light or RF energy, causing an increase in the particle's temperature. A rapid increase in temperature may cause the particle to expand and create an acoustic wave, which may be detected by the detector 1750. Alternatively, rapid heating of the particle above the boiling point of the surrounding liquid may cause a gas bubble, the collapse of which upon cooling may produce a detectable acoustic wave from cavitation. In another example, an increase in temperature may cause degradation or a change in conformation of the particle, allowing some material, such as a fluorophore or contrast agent, to be released from a cavity inside the particle, the fluorescence of which may be detected by the detector 1750.

"Quenching fluorescence" is another type of thermal modulation that may also be used to modulate the response signal 1752. Quenching, which refers to any process which decreases the fluorescence intensity of a given substance, is often heavily dependent on pressure and temperature. Förster resonance energy transfer (FRET), Fluorescence resonance energy transfer (FRET), resonance energy transfer (RET) or electronic energy transfer (EET), are mechanisms describing energy transfer between two chromophores and are all quenching mechanisms. A donor chromophore, initially in its electronic excited state, may transfer energy to an acceptor chromophore through nonradiative dipole-dipole coupling. The efficiency of this energy transfer is inversely proportional to the distance between donor and acceptor. The application of thermal energy may cause the chromophore pairs to pop apart or otherwise separate, thereby permitting each chromophore to fluoresce. This technique may be used to modulate the response signal 1752, in one example, by configuring the chromophore particles to couple together when bound to an analyte. Thermal, acoustic, magnetic or other energy, may also be used to cause the reversible thermal denaturation or modulation of an aptamer or protein complex, where there is one bright confirmation and one quenched confirmation.

In another embodiment, an external energy, such as a magnetic field, may be used to spatially modulate the particles to differentiate the analyte response signal from the unbound particle signal and background noise. Some type of external energy may be applied to the subsurface vasculature 1730 to cause some type of observable movement or motion in the bound particles 1742, i.e., linear motion, rotation, etc. If a particle is bound to or interacting with a target analyte, its physical motion will be affected in response to the modulation 1772, for example, it may translate or rotate slower than unbound particles. Thus, bound particles 1742 will behave differently than the unbound particles 1744 and any other objects present in the body. Alternatively, the particles' response once released from the modulation 1772 may also be observed. For example, bound particles 1742 may take longer to return to normal velocity or normal rotation than unbound particles 1744 once the modulation source 1770 is turned off.

Time-domain separation may also be used to modulate the response signal 1752. For example, modulation may be achieved by exploiting the varying fluorescence lifetimes of different fluorophores. The exponential decay in fluorescence of a particular fluorophore can be observed upon extinguishing the excitation light. In one example, functionalized particles may be composed from or include a fluorescent material that has a much longer fluorescence lifetime than the fluorescence lifetime of those objects that make up the background signal. Upon extinguishing the excitation signal, the system will delay detection of the signal generated by the bound particles 1742 until after the decay of the background fluorescence, thereby allowing the analyte response signal to be distinguished from the background. Fluorescence of the bound particles 1742 may also be modulated by driving the excitation light at certain frequencies or by exploiting the phosphorescence or chemiluminescence lifetimes of different particles. In another example, time-of-flight or a time-of-flight camera may be used to detect a modulated response signal 1752.

In another embodiment, optical analytical methods can be used to modulate the response signal 1752. For example, confocal microscopy may be used to eliminate or diminish the background signal by selecting photons that originate only from a sharp focal area. To this end, bound particles 1742 may be mechanically modulated in and out of the focal area to achieve a periodically modulated fluorescence signal. Other optical techniques may be used for eliminated or reducing characteristics of the background, such as, optical coherence tomography (OCT), wavelength filtering, polarization, phase conjugate despeckling, and phase contrast.

In another embodiment, nuclear magnetic resonance (NMR) may be used to modulate the response signal 1752. Both frequency of precession and magnetic relaxation lifetimes techniques may be used to measure the response of the bound particles 1742 themselves or of their surrounding environment. In general, an RF field is applied to the subsurface vasculature 1730, causing it to emit a magnetic resonance signal at a certain frequency. The characteristics of the particles or other objects in the sample, or the surrounding environment, are observed as they return/relax to their lower energy state. The behavior of bound particles 1742 will be different than the unbound particles 1744 and the background.

The elements of the system, namely the type of applied modulation 1772, the type/shape/materials of particles 1740, types of functionalized receptors and target analytes may all be interrelated. Ultimately, the type of particle 1742 and receptor used to detect a particular target analyte 1740 may be dictated, to some extent, by the characteristics of the target analyte (i.e., type, size, shape, affinities, etc.), the chosen type of modulation 1772 (i.e., spatial, spectral, thermal, magnetic, mechanical, chemical, etc.), and the mode of interrogation (optical, acoustic, magnetic, RF, etc.). Combinations of all of the above modulation techniques may also be used.

Figure 18:
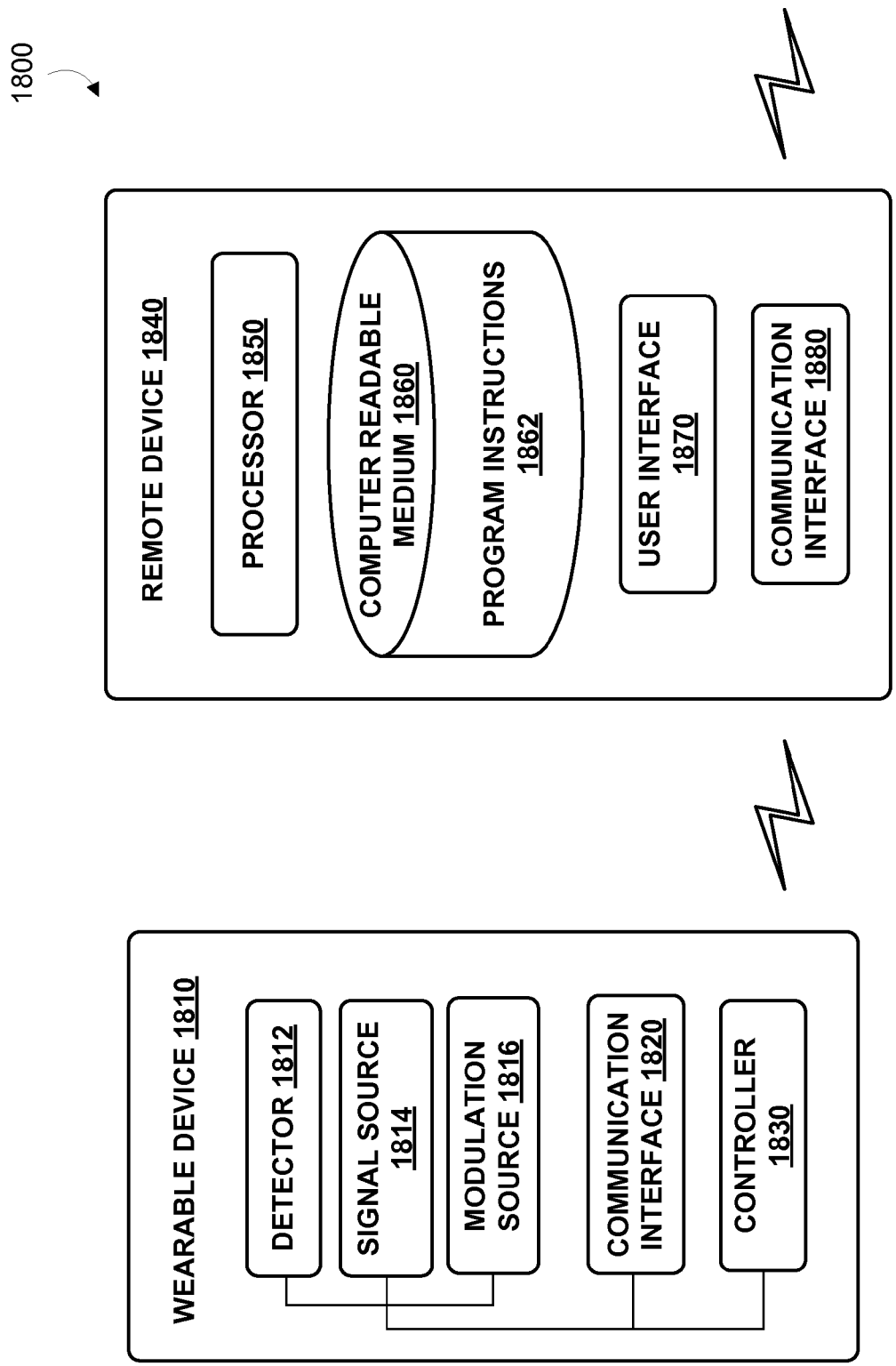
FIG. 18 is a functional block diagram of an example system including a wearable device and a remote device.

FIG. 18 is a simplified block diagram illustrating the components of an example system 1800, including a wearable device 1810. Wearable device 1810 may take the form of or be similar to one of the wrist-mounted devices 200, 300, 400, 500, 600, or 1710 shown in FIGS. 2A-B, 3A-3C, 4A-4C, 5, 6 and 17A-17B. However, wearable device 1810 may also take other forms, such as an ankle, waist, ear, eye or chest-mounted device. Further, any of devices 200, 300, 400, 500, 600 and 1710 may be configured similar to or include any of the components of system 1800, including wearable device 1810.

In particular, FIG. 18 shows an example of a system 1800 including a wearable device 1810 having a detector 1812, in some examples, a signal source 1814, a modulation source 1816, and a communication interface 1820, controlled by a controller 1830. Communication interface 1820 may include an antenna. The components of the wearable device 1810 may be disposed on a mount (not shown) for mounting the device to an external body surface where a portion of subsurface vasculature is readily observable. System 1800 may further include a remote device 1840 in communication with the wearable device 1810, including a processor 1850, a computer readable medium 1860, a user interface 1870, and a communication interface 1880 for communicating with the wearable device 1810 and/or for transmitting data to a server or other remote computing device. While FIG. 18 depicts various components of system 1800 disposed on the wearable device 1810 or the remote device 1840, one of ordinary skill in the art would understand that different configurations and designs are possible, including where all of the components are provided on the wearable device.

Processor 1850 may be a general-purpose processor or a special purpose processor (e.g., digital signal processors, application specific integrated circuits, etc.) and can be configured to execute computer-readable program instructions 1862 that are stored in the computer readable medium 1860 and are executable to provide the functionality of a system 1800 as described herein. The computer readable medium 1850 may include or take the form of one or more non-transitory, computer-readable storage media that can be read or accessed by the processor 1850, and can include volatile and/or non-volatile storage components, such as optical, magnetic, organic or other memory or disc storage, which can be integrated in whole or in part with the processor 1850. The controller 1830 may be configured to operate one or more of the detector 1812, signal source 1814 and modulation source 1816. For example, the controller 1830 may activate the detector 1812, signal source 1814 and modulation source 1816 during each of the pre-set measurement periods.

The program instructions 1862 stored on the computer readable medium 1860 may include instructions to perform or facilitate some or all of the system functionality described herein. For instance, in the illustrated embodiment, program instructions 1862 may include instructions for controller 1830 to operate the detector 1812, signal source 1814 and modulation source 1816. Program instructions 1862 may further cause the processor 1850 to detect the one or more target analytes by differentiating the analyte response signal from the background signal based, at least in part, on a modulation applied by the modulation source 1816. In some cases, the processor may further be configured to differentiate the analyte response signal from the unbound particle signal. Further, the processor 1850 may be configured to determine the concentration of a particular target analyte in the blood from, at least in part, the analyte response signal. The detection and concentration data processed by the processor may be communicated to the patient, for example via the user interface 1870, transmitted to medical or clinical personnel, locally stored or transmitted to a remote server, the cloud, and/or any other system where the data may be stored or accessed at a later time. The program instructions 1862 may also include instructions for operating a user interface 1870, for example, instructions for displaying data transmitted from the wearable device 1810 and analyzed by the processor 1850, or for generating one or more alerts.

Figure 19:
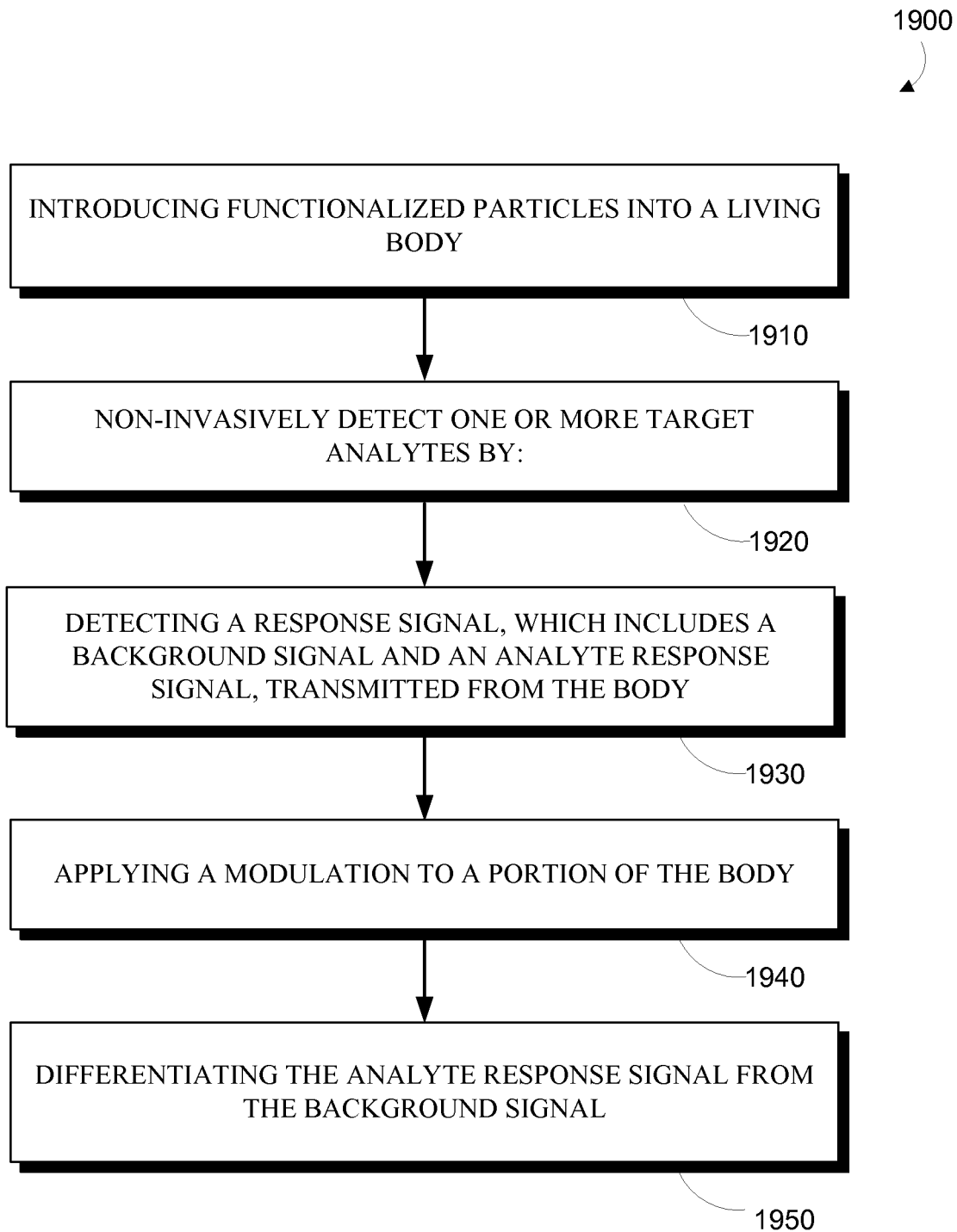
FIG. 19 is a flowchart of an example method for detecting one or more analytes by modulating an analyte response signal.

VIII. Illustrative Method For Modulation of a Response Signal to Distinguish Between Analyte and Background Signals FIG. 19 is a block diagram of an example method (1900) for modulating a response signal. Functionalized particles are introduced into a living body, such as, into a lumen of subsurface vasculature (1910). The particles may be introduced into the blood or some other bodily fluid or system, including the lymphatic system, the digestive system, the nervous system, etc. The functionalized particles may also be embedded in skin or tissue of the body and may be configured to interact with target analytes present in the skin or tissue. Introduction of the functionalized particles into the body may be achieved by any of the means described above, including transdermally, transmucosally, topically, intravenously, intramuscularly, and orally. For example, functionalized particles may be introduced into the blood through use of a swallowable capsule designed to deliver functionalized particles into the intestinal wall.

The functionalized particles may be configured to interact with one or more target analytes present in the body, such as those present in the blood circulating in subsurface vasculature. The particles may take any of the forms or have any of the characteristics, or combinations thereof, described above. In general, the particles will be inherently designed to interact with a particular type target analyte or be functionalized with a receptor that has a specific affinity for a target analyte. A plurality of types of functionalized particles may be introduced into the body, each type having an affinity for a specific target analyte.

According to the example method (1900), the one or more target analytes may be detected (1920) by, in a first step, detecting a response signal transmitted from the body, which includes a background signal and an analyte response signal (1930). The analyte response signal is related to interaction of the functionalized particles with the one or more target analytes. In some examples, the response signal is transmitted from the subsurface vasculature. As described above, in some cases, an interrogating signal may also be directed into the body. The response signal, in such cases, may be generated, at least in part, in response to the interrogating signal and may then be detected. A modulation, configured to alter the response signal such that the analyte response signal is affected differently than the background signal, may be applied to a portion of the body (1940), such as the subsurface vasculature. The analyte response signal may then be differentiated from the background signal (1950).

The response signal may further include an unbound particle signal related to functionalized particles that are not interacting with the one or more target analytes. In some examples, the modulation may also be configured to alter the response signal such that the analyte response signal is affected differently than the unbound particle signal and the background signal, thereby allowing the analyte response signal to be differentiated from the unbound particle signal and the background signal.

The modulation may be configured to alter the response signal by spatially modulating the functionalized particles that are interacting with the one or more target analytes. In other examples, the modulation may be configured to alter the response signal by modulating optical properties of those functionalized particles that are interacting with the one or more target analytes, including their fluorescence, luminescence or chemiluminescence. In other examples, the modulation may be configured to alter the response signal by modulating magnetic, electric, acoustic and/or physical properties of those functionalized particles that are interacting with the one or more target analytes.

Figure 20A:
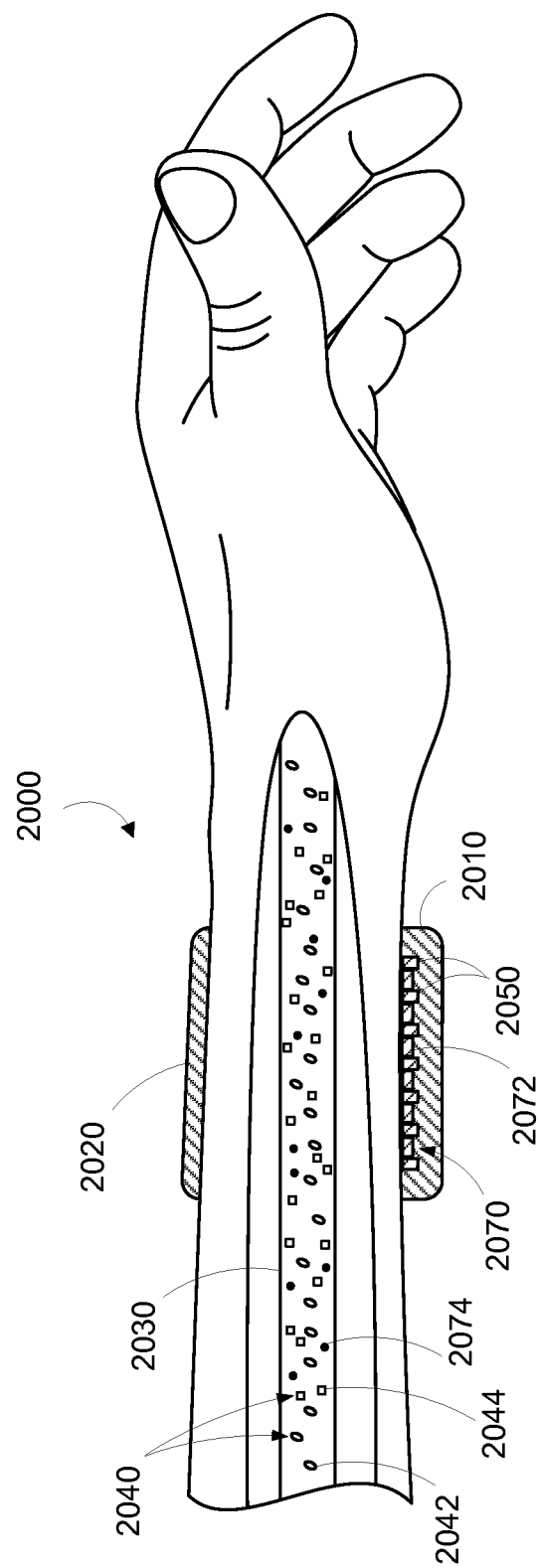
FIG. 20A is side partial cross-sectional view of a wearable device, while on a human wrist, illustrating use of an example modulation source.

IX. Illustrative System and Method For Spatial Modulation of a Response Signal By an External Magnetic Field Using Magnetic Particles FIGS. 20A-20E illustrate one embodiment of an illustrative system 2000 for spatially modulating a response signal. The example system 2000 includes functionalized particles 2040 configured to interact with one or more target analytes present in blood or other bodily fluid, one or more detectors 2050 configured to detect a response signal 2052 transmitted from a portion of the body, such as the subsurface vasculature 2030, and a modulation source 2070 configured to modulate the response signal 2052. The functionalized particles 2040 may be introduced into the body, for example, into a lumen of the subsurface vasculature 2030 by one of the means discussed above. As illustrated in FIG. 20A, the detector(s) 2050 and the magnetic field source(s) 2072 may respectively be provided as an array of connected elements, the utility of which will be described further below. Alternatively, the detector(s) 2050 and the magnetic field source(s) 2072 may each be provided as single elements.

Similar to system 1700 described above, the system 2000 may be implemented with a wearable device 2010, which may include any device that is capable of being worn at, on or in proximity to a body surface, such as a wrist, ankle, waist, chest, or other body part. In the example shown in FIG. 20A, which is a partial cross-sectional side view of a human wrist, the wearable device 2010 may be provided as a wrist-mounted device. A mount 2020, such as a belt, wristband, wristwatch, ankle band, headband, eyeglasses, necklace, earrings, etc. can be provided to mount or stabilize the device at, on or in proximity to the body surface. In the present example, mount 2020 is provided as strap or wristband to secure the device 2010 on a wearer's wrist. As described above with respect to system 1700, system 2000 may also include a processor (not shown) configured to non-invasively detect the presence and/or concentration of the one or more target analytes.

Both bound particles 2042—those functionalized particles interacting with the target analytes—and unbound particles 2044—those functionalized particles not interacting with the target analytes—may be present in the subsurface vasculature 2030 in the area of the wearable device 2010. The modulation source 2070 may include any means for modulating the response signal 2052, which may include an analyte response signal 2054, an unbound particle signal 2056 and a background signal (not shown). For example, the modulation source 2070 may be configured to both modulate the analyte response signal 2054 differently than the unbound particle signal 2056, such that the analyte response signal may be differentiated from the unbound particle signal, and to modulate the analyte response signal 2054 from the background.

Figure 20B:
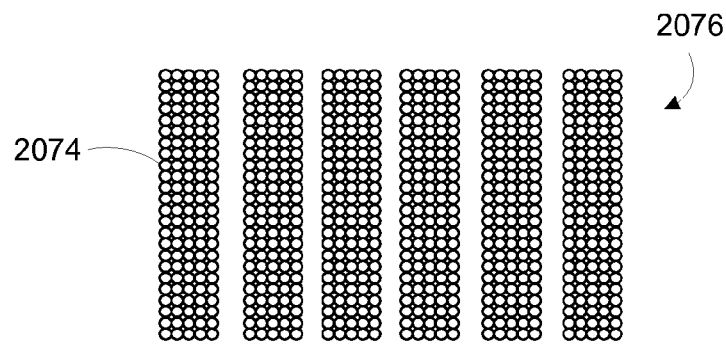
FIG. 20B is a top view of a mask for use in an example system for modulating an analyte response signal.
Figure 20C:
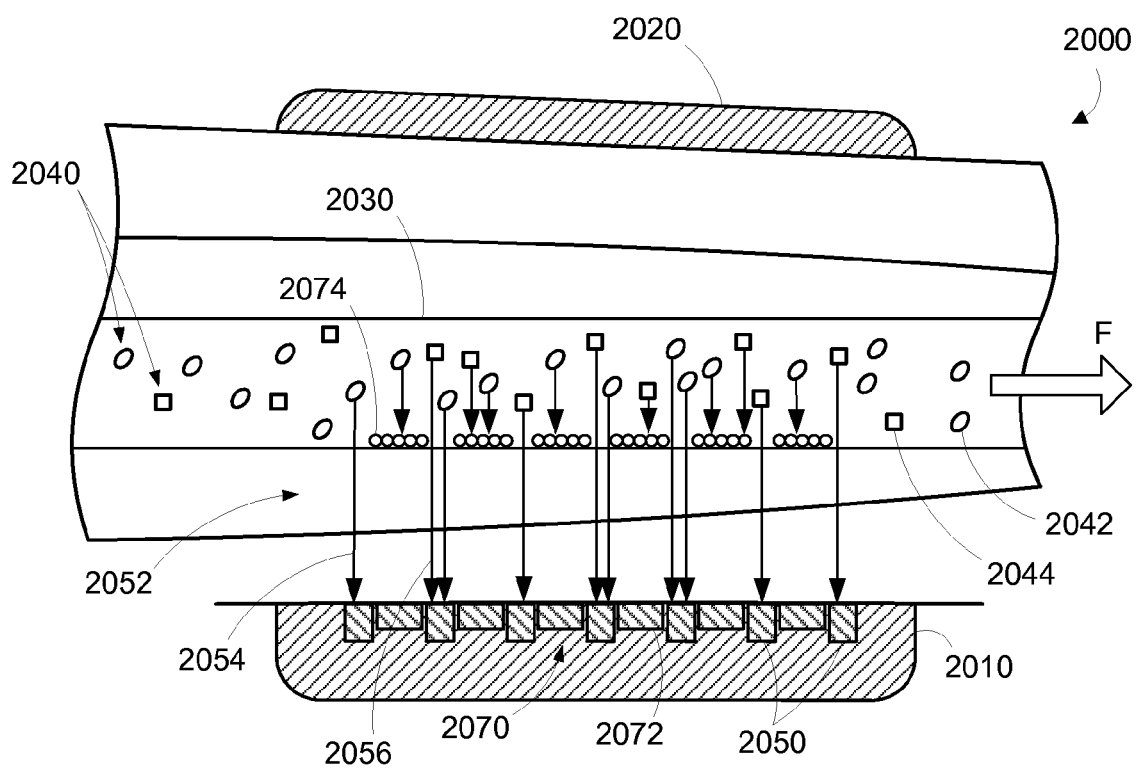
FIG. 20C is a side partial cross-sectional detail view of a wearable device, while on a human wrist, illustrating use of an example modulation source.

As shown in FIGS. 20B and 20C, the modulation source 1770 may be configured to alter the analyte response signal 2054 and the unbound particle signal 2056 by spatially modulating the bound particles 2042 and the unbound particles 2044 with a mask 2076 having a spatial arrangement. The modulation source 2070 may include magnetic particles 2074, introduced into the subsurface vasculature 2030, and one or more magnetic field sources 2072, sufficient to distribute the magnetic particles 2074 into a spatial arrangement in a lumen of the subsurface vasculature 2030. The magnetic field source(s) 2072 may include, for example, an array of permanent magnets, field concentrating materials and shielding materials, or thin film materials.

In one example, the magnetic particles 2074 may be manipulated to form a mask 2076, as shown in FIG. 20B, on an inner surface of the lumen of the subsurface vasculature 2030, for spatial modulation of the response signal 2052. As shown in FIG. 20C, when the magnetic field source(s) 2072 are activated, the magnetic particles 2074 may aggregate in the areas of the concentrated magnetic field(s) on an inner surface of the lumen of the subsurface vasculature 2030 closes to the detector(s) 2050. Accordingly, the shape of the mask may be determined based on the spatial shape or distribution of the magnetic fields created by the magnetic field source(s) 2072. For example, the mask 2076 may be in the shape of several bars oriented essentially perpendicular to the flow of fluid in the vessel (F) and formed by an array of magnetic field sources 2072 of similar shape. In some examples, the bars of the mask 2076 may be spaced up to approximately 1 millimeter apart.

As shown in FIG. 20C, the mask 2076 acts to block or otherwise diminish the response signal 2052 from reaching the detector(s) 2050 in the area in which it forms. When analyte-bound particles 2042, unbound particles 2044, and any other materials (which may create a background signal) pass through the vasculature 2030 over the mask, the intensity of the response signal 2052 will essentially "blink" or pulse. In operation, different materials passing through the vasculature will be of different sizes and shapes and, therefore, will pass through the vasculature 2030 at different speeds. For example, the bound particles 2042 will, in theory, be larger and heavier than the unbound particles 2044. Accordingly, the bound particles 2042 will pass over the mask 2076 at a slower speed than the unbound particles 2044 and, therefore, the analyte response signal 2054 will "blink" at a lower frequency than the unbound particle signal 2056, providing one level of distinction. Moreover, the bound particle signal 2054 will "blink" at a different frequency than the background signal.

Figure 21A:
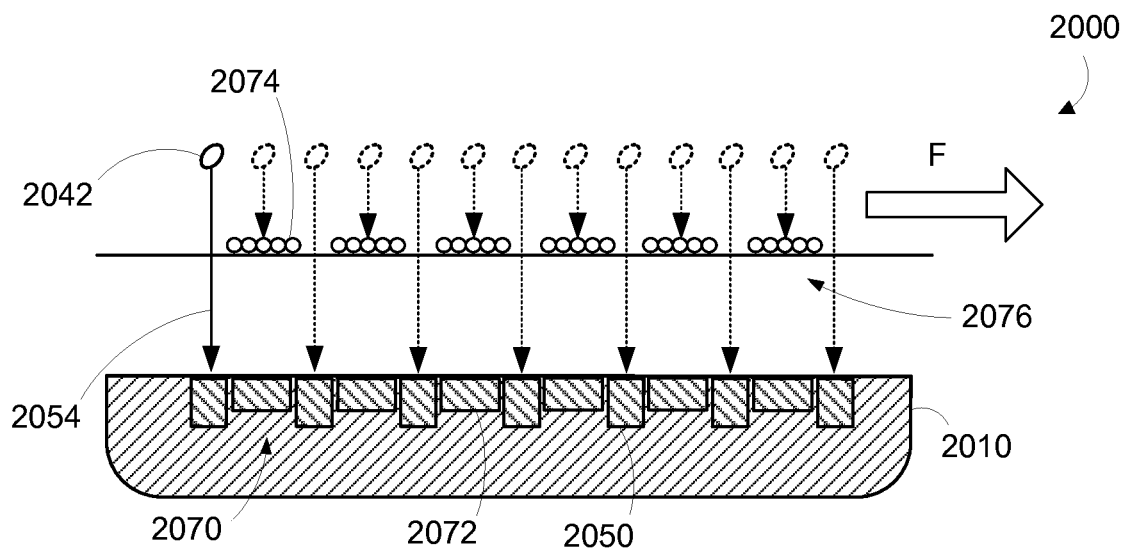
FIG. 21A is a side partial cross-sectional detail view of a wearable device, while on a human wrist, illustrating use of an example modulation source.
Figure 21B:
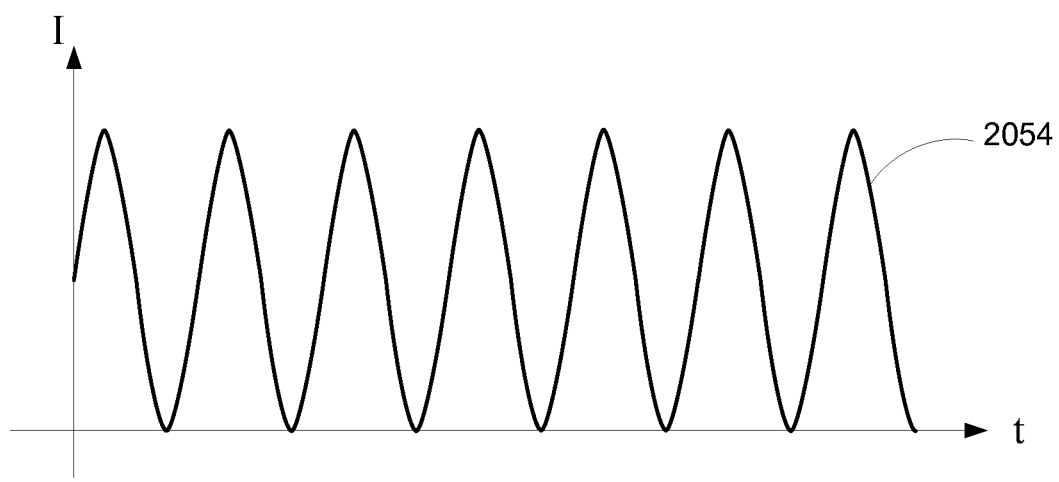
FIG. 21B is a graphical representation of an example modulated analyte response signal.

This concept is also illustrated in FIGS. 21A and 21B, with a single analyte bound particle 2042 passing through the vasculature in the direction of blood flow (F). Moving from left to right in the direction of blood flow (F), the analyte response signal 2054 will initially be detected by a first element of the detector 2050. Depending on the type of particle 2040, the target analyte, and the type of interaction or association between the target analyte and the particle 2040, the analyte response signal 2054 may be of many different types. For example, in embodiments where the particle 2040 includes a fluorophore, or the interaction between the particle and the target analyte generates a fluorescence, the analyte response signal 2054 may be an optical signal. As the bound particle 2042 processes (as shown in dotted lines), the analyte response signal 2054 will then be blocked or diminished by the magnetic particles 2074 forming the mask 2076 in the vasculature, whereby little or no analyte response signal 2054 will reach the detector 2050. Thus, as the bound particle 2042 continues through the vasculature, passing over each segment of the mask 2076, the analyte response signal 2054 will be periodically blocked or diminished, which may be observed as a "blinking" of the signal. Other forces, such as magnetic or acoustic forces, may be used to influence the motion of the particles through the mask area, thereby further distinguishing between particles with different hydrodynamic properties in the blood flow (e.g. large vs., small, bound vs. unbound, shapes, buoyancy and the like).

FIG. 21B is a graphical representation of the analyte response signal 2054 intensity (I) plotted against time (t). This Figure is illustrative of the "blinking" signal which may be sensed by the detector 2054. In operation, different items present in the vasculature, i.e., unbound particles 2044, cells, other molecules, will "blink" at a different frequency, producing a different signal, having a different period. To this end, bound particles 2042 may be differentiated from other objects present in the blood.

In the embodiments shown in FIGS. 20A-20C and 21A-21B, a mask 2076 is formed on the inside of a vessel 2030 by manipulating magnetic particles 2074, introduced into the subsurface vasculature, with an external magnetic field source 2072. By forming the mask on the inside of the vessel, dispersion caused by intervening tissue, which might otherwise occur if the mask were placed external to the body, may be reduced. Periodic mechanical (e.g. acoustic) perturbation may "sharpen" the bands of the mask by adding energy to reduce non-specific aggregation of the magnetic particles.

Figure 22:
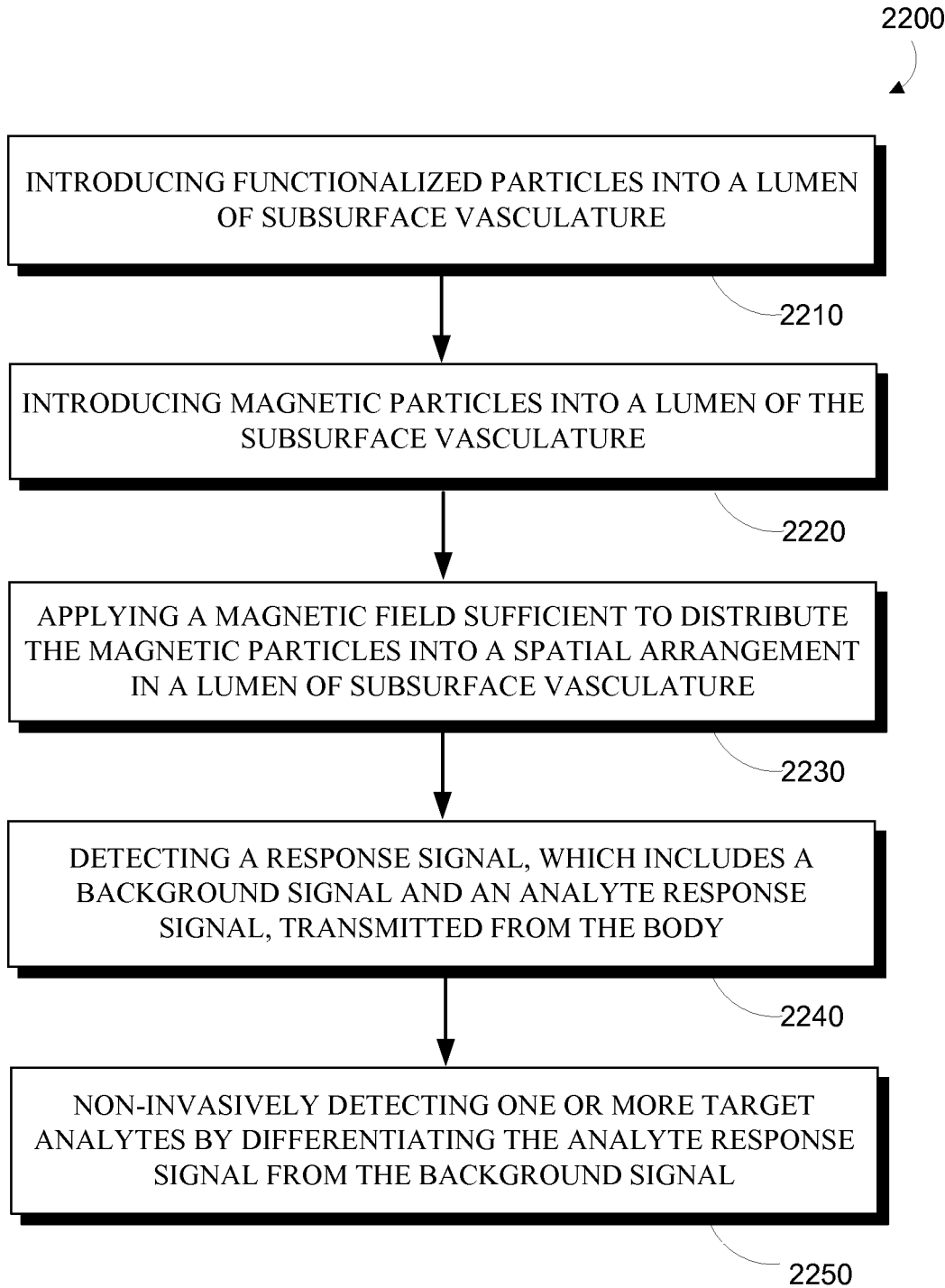
FIG. 22 is a flowchart of an example method for detecting one or more analytes by modulating an analyte response signal.

FIG. 22 is a flow chart of an exemplary method 2200 for analyte detection by spatially modulating are response signal with an internally applied mask. In a first step, functionalized particles are introduced into a lumen of subsurface vasculature (2210). The functionalized particles may be configured to interact with one or more target analytes present in blood (or other body fluid) circulating in the subsurface vasculature (or other body system). Magnetic particles may also be introduced into the subsurface vasculature (2220) and a magnetic field, sufficient to distribute the magnetic particles into a spatial arrangement in a lumen of the subsurface vasculature, may be applied (2230). A response signal, including a background signal and an analyte response signal, transmitted from the subsurface vasculature is detected (2240). The analyte response signal is related to interaction of the functionalized particles with the one or more target analytes and may be modulated with respect to the background signal due, at least in part, to the spatial arrangement of the magnetic particles. The one or more target analytes may be detected by differentiating the analyte response signal from the background signal due, at least in part, to the modulation of the analyte response signal (2250).

The response signal may further include an unbound particle signal related to functionalized particles that are not interacting with the one or more target analytes. The one or more target analytes may be non-invasively detected by differentiating the analyte response signal from the background signal and the unbound particle signal due, at least in part, to the modulation of the analyte response signal. The analyte response signal is modulated differently than the background signal, in some cases, due, at least in part, to the velocity of the functionalized particles in the blood circulating in the subsurface vasculature. The analyte response signal may also be modulated differently than the unbound particle signal, in some cases, due, at least in part, to a difference in the velocity of the functionalized particles in the blood circulating in the subsurface vasculature and the velocity of the unbound functionalized particles.

X. Illustrative System and Method For Spatial Modulation of a Response Signal Using a Mask External to The Vasculature In another example system 2300, shown in FIGS. 23A and 23B, the modulation source 2370 may employ a signal-blocking or diminishing mask 2476 placed externally to the subsurface vasculature 2330. The mask 2476 may be positioned anywhere between the subsurface vasculature 2330 or other body system or tissue in which the functionalized particles 2340 have been introduced and a detector 2350, for example, against an external surface of the body, imbedded in the skin or other tissue, or applied directly to the surface of the detector 2350. Detector 2350 may be provided as part of a wearable device 2310, which may include a mount 2330, such as a strap for holding the device 2310 against a body surface, such as a wrist. Similar to mask 2076 used in system 2000 as shown in FIG. 20B, mask 2476 may be configured to alter the analyte response signal 2354 and the unbound particle signal 2356 by spatially modulating the bound particles 2342 and the unbound particles 2344 with a mask 2476 having a spatial arrangement. For example, the mask 2476 may be in the shape of several bars oriented essentially perpendicular to the flow of fluid in the vessel (F) that are spaced up to approximately 1 millimeter apart.

Figure 23A:
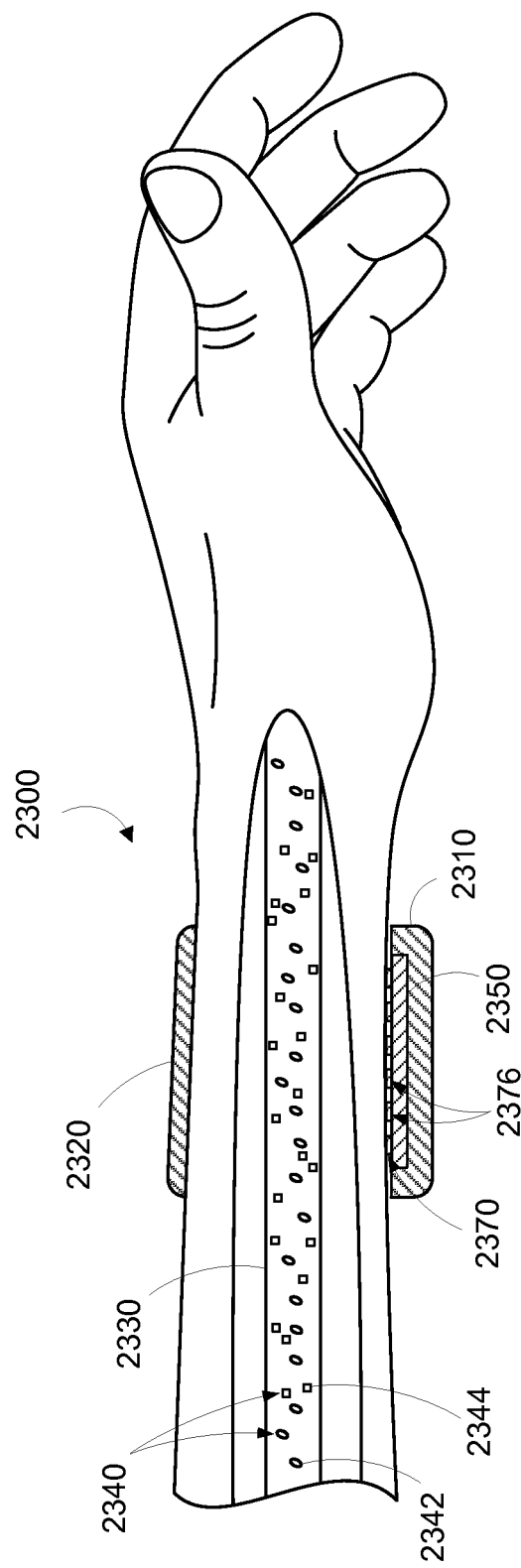
FIG. 23A is side partial cross-sectional view of a wearable device, while on a human wrist, illustrating use of an example modulation source.
Figure 23B:
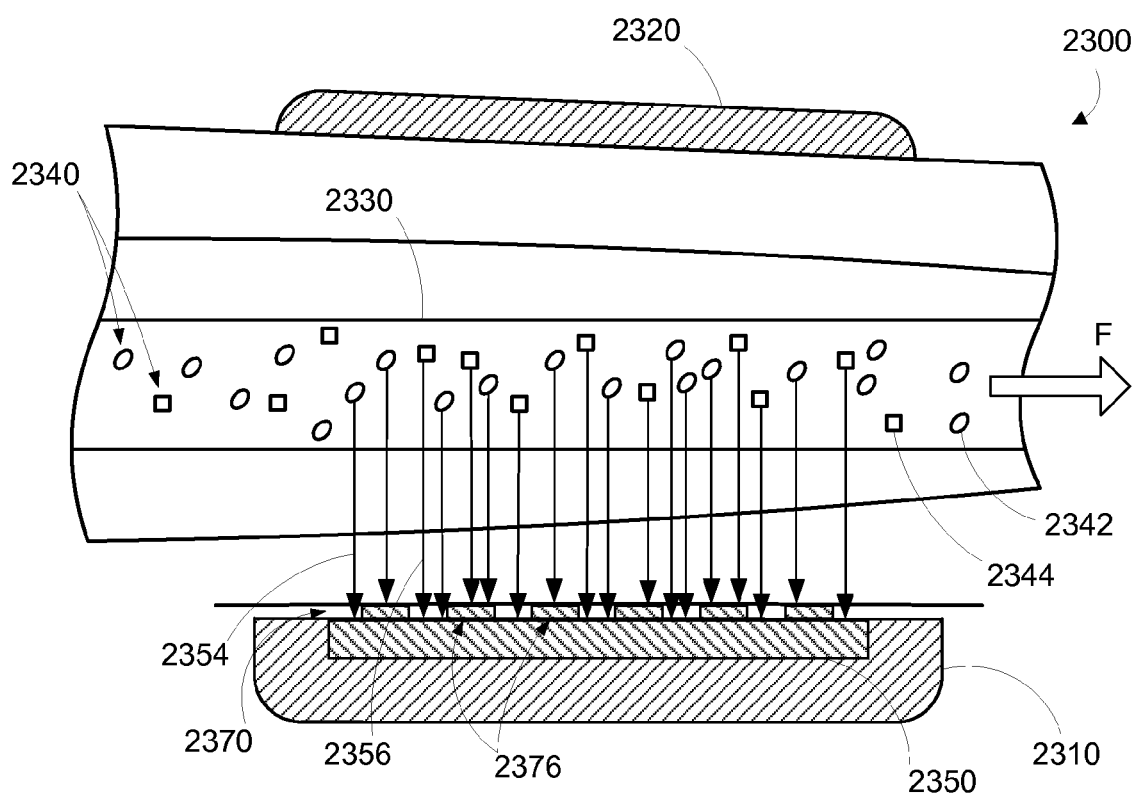
FIG. 23B is a side partial cross-sectional detail view of a wearable device, while on a human wrist, illustrating use of an example modulation source.

As shown in FIG. 23B, the external mask 2476 may prohibit or diminish the analyte response signal 2354, the unbound particle signal 2356 and any background signal (not shown) from reaching the detector 2350. Similar to the discussion provided above with respect to system 2000, the spatial arrangement of the mask 2476 acts to modulate the analyte response signal 2354 with respect to the background signal and/or the unbound particle signal 2356. Because the bound particles 2342 will have different hydrodynamic properties than the unbound particles 2344 and those objects that produce the background signal, the bound particle signal 2354 will be modulated differently than the unbound particle signal 2356 and/or the background signal. The one or more target analytes may be detected by differentiating the analyte response signal 2354 from the background signal due, in least in part, to the modulation of the analyte response signal 2354 by the mask 2376.

In another example illustrated in FIGS. 24A and 24B, the functionalized particles 2440 of system 2400 may be magnetic. As described above, the functionalized magnetic particles 2440 may be formed of a magnetic material (i.e., a material that responds to a magnetic field) or may be functionalized with a magnetic material. The modulation source 2470 may employ a signal-blocking or diminishing mask 2476 placed externally to the subsurface vasculature 2430 and may include an external magnetic field source 2472. The external magnetic field source 2472 may be positioned on a wearable device 2410, such as a wrist-mountable device, having a mount 2420 for securing the device against a body surface, along with a detector 2450. In operation, a magnetic field may be applied by magnetic field source 2472 to the subsurface vasculature 2430 sufficient to draw the functionalized magnetic particles towards the surface of the lumen of subsurface vasculature 2430 closest to the mask, as shown in FIG. 24B.

As compared to using an external mask, by using an internal mask, the response signal may be modulated at a location that has less scattering medium between the source (i.e., the functionalized particles) and the point of modulation (i.e., the mask). With an internal mask, the unmodulated light is scattered by blood but not by vasculature wall and skin. As shown in FIGS. 20A-20C, light traveling from the particles 2040, both bound 2042 and unbound 2044, to the detector 2050 is spatially scattered by the dispersive tissue (blood, vein, skin) that is present between particle and detector, which may reduce the signal to noise ratio. With an external mask as shown in FIGS. 23A and 23B, both the unmodulated and the modulated light may be scattered by blood, vasculature wall and skin. This scattering may be mitigated, as shown in FIG. 24B, by moving the particles towards the most superficial surface of the vein (e.g., closer to the detector 2450), as described with respect to system 2400, so as to eliminate most of the scattering from blood, which is a larger contributor to scattering than tissue. Acoustic, magnetic or other forces may be used to move particles towards the most superficial wall of the vasculature.

As an alternative to using a physical mask (either internal or external), spatial modulation may be achieved with structured illumination or structured detection. In the case of structured illumination, light stripes or spots generated with spaced apart light sources (LEDs or laser diodes, e.g.) or scanned light lines or projected light patterns, combined with broad detection may achieve spatial modulation of the particle response signal. With a structured detection technique, a broad illumination source is used in combination with spatially separated line or point detectors, or a pixelated detector array. Combinations of all of the above techniques may also be used.

In another embodiment shown in FIGS. 25A and 25B, system 2500 may employ magnetic functionalized particles 2540 and a modulation source 2570 having a signal-blocking or diminishing mask 2576 placed externally to the subsurface vasculature 2530, similar to system 2400. Magnetic field source 2572, in this example, may be positioned on a wearable device 2510, such as a wrist-mountable device, having a mount 2520 for securing the device against a body surface, upstream from the detector 2550, at a point A. Using an external magnetic field generated by magnetic field source 2572, the functionalized particles 2540 may be retained against the upper wall of the vein for some amount of time at a point A and then released back into the blood flow. The response signal from the particles, including the analyte response signal 2554, the unbound particle signal 2556 and the background signal (not shown), may be detected a short distance downstream from their point of release (so that they are still close to the vein wall, but have picked up velocity in the blood stream) at a point B. The response signal may be spatially modulated by the mask 2576, which may act to distinguish the bound particles 2542 and unbound particles 2544, having different hydrodynamic properties, on the basis of speed. After the magnetic field source 2572 is deactivated and the particles are released, the resulting speed of the bound particles 2542 will be different, and therefore detectable, over the speed of the unbound particles 2544 and other objects in the blood.

Figure 26:
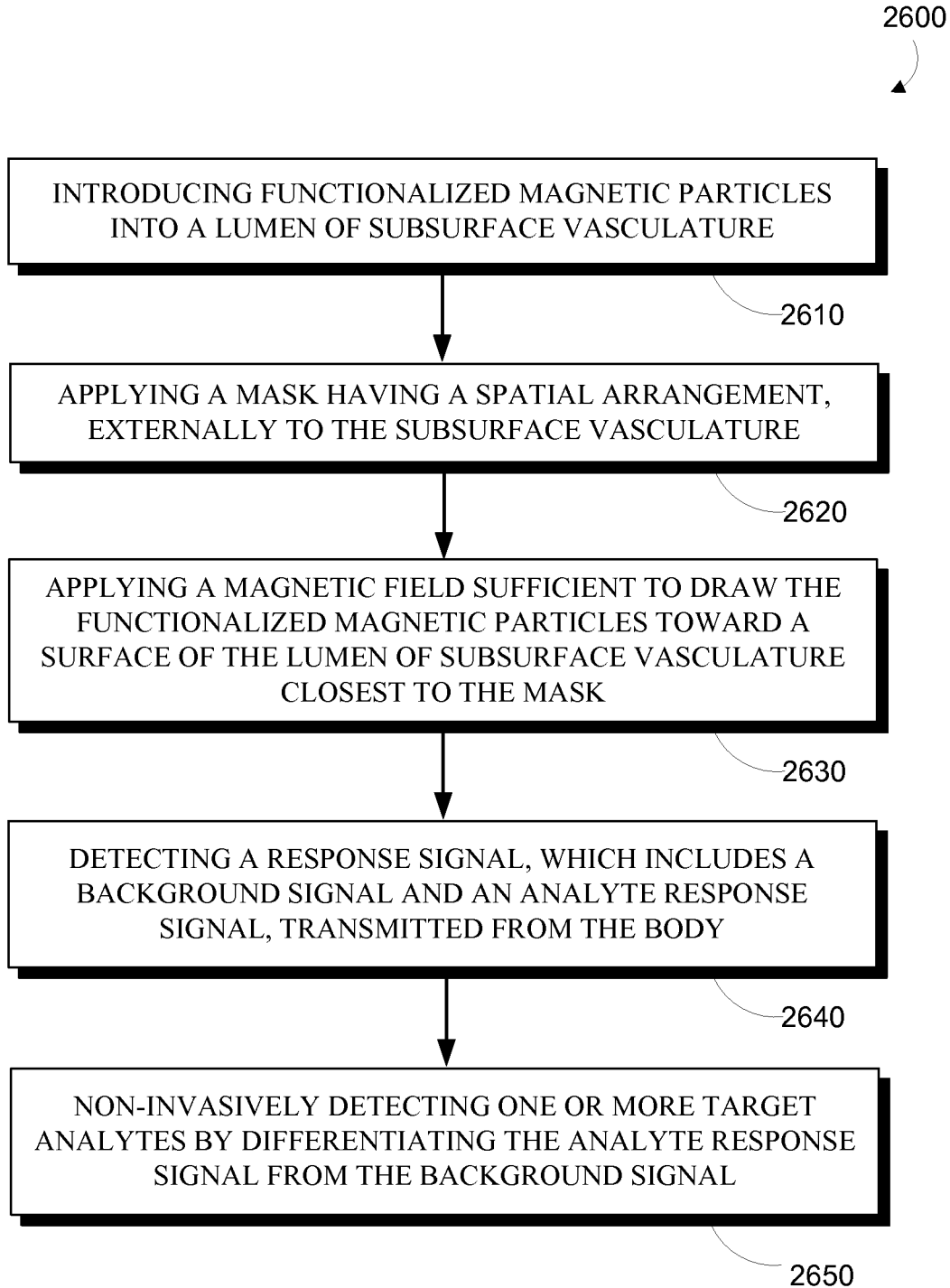
FIG. 26 is a flowchart of an example method for detecting one or more analytes by modulating an analyte response signal.

FIG. 26 is a flow chart of an exemplary method 2600 for analyte detection by spatially modulating a response signal with an externally applied magnetic field. Functionalized magnetic particles configured to interact with one or more target analytes present in blood circulating in the subsurface vasculature are introduced into a lumen of subsurface vasculature (2610). A mask, having a spatial arrangement, is applied externally to the subsurface vasculature (2620). A magnetic field sufficient to draw the functionalized magnetic particles towards a surface of the lumen of subsurface vasculature closest to the mask is applied (2630). A response signal, which includes a background signal and an analyte response signal, transmitted from the subsurface vasculature may be detected (2640). The analyte response signal is related to interaction of the functionalized magnetic particles with the one or more target analytes and is modulated with respect to the background signal due, at least in part, to the spatial arrangement of the mask. The one or more target analytes may be non-invasively detected by differentiating the analyte response signal from the background signal due, at least in part, to the modulation of the analyte response signal (2650). In some examples, an interrogating signal may also be directed into the subsurface vasculature and a response signal transmitted from the subsurface vasculature in response to the interrogating signal may be detected.

The response signal may further include an unbound particle signal related to functionalized particles that are not interacting with the one or more target analytes. The target analytes may be detected by differentiating the analyte response signal from the background signal and the unbound particle signal due, at least in part, to the modulation of the analyte response signal. The analyte response signal may be modulated differently than the background signal. Additionally or alternatively, the analyte response signal may be modulated differently than the unbound particle signal.

In other exemplary methods, the magnetic field may be applied at a first location with respect to the subsurface vasculature and the mask may be applied at a second location with respect to the subsurface vasculature. The second location may be downstream of the first location in the direction of the flow of blood circulating in the subsurface vasculature. In such methods, the magnetic field may subsequently be deactivated and a response signal transmitted from the subsurface vasculature may be detected at the second location.

XI. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system, comprising:
    functionalized particles, wherein the functionalized particles interact with one or more target analytes present in an environment;
    a detector positioned in proximity to the environment and that detects a response signal transmitted from the environment, wherein the response signal includes a background signal and an analyte response signal indicative of interaction of the one or more target analytes with the functionalized particles;
    magnetic particles;
    a magnetic field source positioned in proximity to the environment and configured to distribute the magnetic particles into a spatial arrangement in the environment such that the magnetic particles in the spatial arrangement are positioned in proximity to a surface of the environment nearest to the detector, wherein the spatial arrangement of the magnetic particles in the environment modulates the analyte response signal as functionalized particles in the environment flow past the spatial arrangement of magnetic particles, such that the analyte response signal is affected differently than the background signal, such that a period of the unmodulated analyte response signal is different than a period of the modulated analyte response signal as detected, and such that the period of the modulated analyte response signal as detected is different than a period of the background signal as detected; and a processor configured to non-invasively detect the one or more target analytes by differentiating the analyte response signal from the background signal, based at least in part, on the modulation of the analyte response signal.

2. The system of claim 1, wherein the response signal further includes an unbound particle signal indicative of functionalized particles that are not interacting with the one or more target analytes.

3. The system of claim 2, wherein the processor further non-invasively detects the one or more target analytes by differentiating the analyte response signal from the unbound particle signal, at least in part, based on modulation of the signals due, at least in part, to the spatial arrangement of the magnetic particles.

4. The system of claim 3, wherein the analyte response signal is affected differently than the unbound particle signal, and wherein a period of the modulated analyte response signal as detected is different than a period of the modulated unbound particle signal as detected.

5. The system of claim 1, further comprising an interrogating signal source, the response signal being transmitted in response to the interrogating signal.

6. The system of claim 1, wherein the environment comprises a fluid conduit.

7. The system of claim 1, wherein the environment comprises a fluid reservoir.

8. The system of claim 1, wherein the environment comprises a living body.

9. The system of claim 8, wherein the environment comprises a lumen of subsurface vasculature in the living body.

\* \* \* \* \*